US010444232B2

(12) United States Patent
Guo et al.

(10) Patent No.: US 10,444,232 B2
(45) Date of Patent: Oct. 15, 2019

(54) DIAGNOSTIC DEVICES, SYSTEMS, AND METHODS

(71) Applicant: The Trustees of Columbia University in the City of New York, New York, NY (US)

(72) Inventors: Tiffany Guo, Lagrange, OH (US); Samuel K. Sia, New York, NY (US); Jeisun Shi Xie, San Jose, CA (US); Fanxing Meng, Tianjin (CN); Keith Yeager, Jersey City, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/503,512

(22) PCT Filed: Aug. 13, 2015

(86) PCT No.: PCT/US2015/045034
§ 371 (c)(1),
(2) Date: Feb. 13, 2017

(87) PCT Pub. No.: WO2016/025698
PCT Pub. Date: Feb. 18, 2016

(65) Prior Publication Data
US 2017/0227537 A1    Aug. 10, 2017

Related U.S. Application Data

(60) Provisional application No. 62/036,987, filed on Aug. 13, 2014, provisional application No. 62/077,782, filed on Nov. 10, 2014.

(51) Int. Cl.
*G01N 33/543* (2006.01)
*B01L 3/00* (2006.01)
(Continued)

(52) U.S. Cl.
CPC .... *G01N 33/54366* (2013.01); *B01L 3/50273* (2013.01); *B01L 3/502715* (2013.01);
(Continued)

(58) Field of Classification Search
CPC ........... B01L 2200/16; B01L 2300/023; B01L 2300/0654; B01L 2300/0816;
(Continued)

(56) References Cited

U.S. PATENT DOCUMENTS 5,074,765 A   12/1991  Pekar
5,450,856 A    9/1995  Norris
(Continued)

FOREIGN PATENT DOCUMENTS

EP       0249418 A2    12/1987
WO    2011141908 A2    11/2011
WO    2014042979 A1     3/2014

OTHER PUBLICATIONS

Addae-Mensah et al., "Actuation of elastomeric microwaves in point-of-care settings using handheld, battery-powered instrumentation," Lab Chip, vol. 10, pp. 1618-1622, Apr. 2010.
(Continued)

*Primary Examiner* — Jennifer Wecker
(74) *Attorney, Agent, or Firm* — Potomac Law Group, PLLC; Mark Catan

(57) ABSTRACT

Diagnostic systems, methods, and devices employing low-cost handheld components are disclosed herein. A diagnostic system can include a diagnostic device that is configured to perform one or more assays on a fluid sample, such as a whole blood sample, in one or more microfluidic channels or chambers. The diagnostic device can move the fluid sample into or through the one or more microfluidic channels or chambers without using any electrical power, for example, using manual actuation to generate a positive or negative
(Continued)

pressure within the diagnostic device. The diagnostic device can have a connector for interfacing with a separate handheld unit that can provide power and data processing. For example, the separate handheld unit can be a smartphone or PDA, and the connector can interface with an existing input/output port of the unit to draw power and/or transmit data.

24 Claims, 12 Drawing Sheets

(51) Int. Cl.
    *G01N 33/569*     (2006.01)
    *G01N 33/571*     (2006.01)
    *G01N 33/58*     (2006.01)
    *G01N 33/68*     (2006.01)
    *G01N 33/66*     (2006.01)

(52) U.S. Cl.
    CPC ..... *G01N 33/56988* (2013.01); *G01N 33/571* (2013.01); *G01N 33/58* (2013.01); *G01N 33/66* (2013.01); *G01N 33/6827* (2013.01); *B01L 2200/16* (2013.01); *B01L 2300/023* (2013.01); *B01L 2300/0654* (2013.01); *B01L 2300/0816* (2013.01); *B01L 2400/049* (2013.01); *B01L 2400/0481* (2013.01)

(58) Field of Classification Search
    CPC ....... B01L 2400/0481; B01L 2400/049; B01L 3/502715; B01L 3/50273; G01N 33/54366; G01N 33/56988; G01N 33/571; G01N 33/58; G01N 33/66; G01N 33/6827
    See application file for complete search history.

(56) References Cited

U.S. PATENT DOCUMENTS

| | | | |
|---|---|---|---|
| 6,137,527 | A | 10/2000 | Abdel-Malek et al. |
| 6,716,002 | B2 | 4/2004 | Higashino |
| 6,743,399 | B1 | 6/2004 | Weigl et al. |
| 6,767,194 | B2 | 7/2004 | Jeon et al. |
| 7,284,966 | B2 | 10/2007 | Xu et al. |
| 7,420,659 | B1 | 9/2008 | Cabuz et al. |
| 7,526,741 | B2 | 4/2009 | Lee et al. |
| 7,942,160 | B2 | 5/2011 | Jeon et al. |
| 8,260,551 | B2 | 9/2012 | Janky et al. |
| 8,652,852 | B2 | 2/2014 | Beebe et al. |
| 8,737,971 | B2* | 5/2014 | van Rooyen ........... H04W 4/18 455/414.1 |
| 2004/0183724 | A1 | 9/2004 | Sheynblat |
| 2005/0250995 | A1 | 11/2005 | Quy |
| 2006/0092029 | A1 | 5/2006 | Browne et al. |
| 2006/0252069 | A1 | 11/2006 | Zhang et al. |
| 2007/0082340 | A1 | 4/2007 | Huletsky et al. |
| 2007/0184463 | A1 | 8/2007 | Molho et al. |
| 2008/0023388 | A1 | 1/2008 | Cho et al. |
| 2009/0197275 | A1 | 8/2009 | Schoenbrunner et al. |
| 2009/0220387 | A1 | 9/2009 | Guu et al. |
| 2009/0221431 | A1 | 9/2009 | Yoo |
| 2010/0015634 | A1 | 1/2010 | VanDine et al. |
| 2010/0022186 | A1 | 1/2010 | Walley |
| 2010/0074253 | A1 | 3/2010 | Cheriyath et al. |
| 2010/0152432 | A1 | 6/2010 | Wu |
| 2010/0234237 | A1 | 9/2010 | Yoo |
| 2011/0021374 | A1* | 1/2011 | Lee ........................ G01N 24/08 506/9 |
| 2011/0144451 | A1 | 6/2011 | Robertson |
| 2011/0207619 | A1 | 8/2011 | Ehben et al. |
| 2011/0243790 | A1* | 10/2011 | Cheung .............. G01N 15/0612 422/52 |
| 2011/0251960 | A1 | 10/2011 | Holla et al. |
| 2011/0269138 | A1 | 11/2011 | Wiezer |
| 2013/0171028 | A1 | 7/2013 | Shaffer et al. |
| 2013/0273524 | A1* | 10/2013 | Ehrenkranz ........... G01N 21/17 435/5 |
| 2014/0329225 | A1 | 11/2014 | Morin |

OTHER PUBLICATIONS

Hernandez et al., "Smartphone as a Portable Detector, Analytical Device, or Instrument Interface," Smartphones as an Applied Research Perspective, Chapter 4, pp. 73-91, 2017.
Blaya et al., "Personal digital assistants to collect tuberculosis bacteriology data in Peru reduce delays, errors, and workload, and are acceptable to users: cluster randomized controlled trial," International Journal of Infectious Diseases, vol. 13, 410-418 (2009).
Castro et al., "Novel Point-of-Care Test for Simultaneous Detection of Nontreponemal and Treponemal Antibodies in Patients with Syphilis," J Clin Microbiol, vol. 48, 4615-4619 (2010).
Chin et al., "Mobile device for disease diagnosis and data tracking in resource-limited settings," Clinical Chemistry, Apr. 1, 2013, vol. 59(4), pp. 629-640.
Delaney et al,, "Evaluation of the Performance Characteristics of 6 Rapid HIV Anybody Tests," Clin Infect Dis, vol. 52, 257-263 (2011).
Dimov et al., "Stand-alone self-powered integrated microfluidic blood analysis system (SIMBAS)," Lab on a Chip, vol. 11, 845-850 (2011).
Freifeld et al., "Participatory epidemiology: use of mobile phones for community-based health reporting," PLoS medicine 7, e1000376 (2010).
International Preliminary Report on Patentability for International Application No. PCT/US2015/045034 dated Feb. 23, 2017.
International Search Report and Written Opinion for application No. PCT/US2015/045034, dated Dec. 29, 2015.
Kagulire et al., "Field evaluation of five rapid diagnostic tests for screening of HIV-1 infections in rural Rakai, Uganda," Int J Std Aids, vol. 22, 308-309 (2011).
Kuo et al., "Hijacking Power and Bandwidth From the Mobile Phone's Audio Interface," ISLPED'10 Design Contest, Austin, Texas, 2010.
Kuznik et al., "Antenatal Syphilis Screening Using Point-of-Care Testing in Sub-Saharan African Countries: A Cost-Effectiveness Analysis," PLoS medicine, vol. 10, e1001545 (2013).
Lee et al., "A simple and smart telemedicine device for developing regions: a pocket-sized colorimetric reader," Lab on a Chip, vol. 11, 120-126 (2011).
Meredith et al., "A mobile-phone-based breath carbon monoxide meter to detect cigarette smoking," Nicotine & Tobacco Research, vol. 16, 766-773 (2014).
Mudanyali et al., "Integrated rapid-diagnostic-test reader platform on a cellphone," Lab on a Chip, vol. 12, 2678-2686 (2012).
Nemirosji et al., "Universal Mobile Electrochemical Detector Designed for Use in Resource-Limited Applications," PNAS, 201405679, Aug. 2014.
Oncescu et al., "Cholesterol testing on a smartphone. Lab on a Chip," vol. 14, 759-763 (2014).
Wei et al., "Fluorescent Imaging of Single Nanoparticles and Viruses on a Smart Phone," Acs Nano 7, 9147-9155 (2013).
Yin et al., "A Dual Point-of-Care Test Shows Good Performance in Simultaneously Detecting Nontreponemal and Treponemal Antibodies in Patients With Syphilis: A Muitisite Evaluation Study in China," Clin Infect Dis, vol. 56, 659-665 (2013).
Abate et al., "Syringe-Vacuum Microfluidics: A Portable Technique to Create Monodispers Emulsions," Biomicrofluidics, Mar. 16, 2011, 5(014107): pp. 1-8.
Ferguson et al., "Genetic Analysis of H1N1 Influenza Virus from Throat Swab Samples in a Microfluidic System for Point-of-Care Diagnostics," Journal of the American Chemical Society, Jun. 15, 2011, vol. 133(23), pp. 9129-9135.
International Search Report and Written Opinion dated May 31, 2013 for International Application No. PCT/US2013/023015.

(56) References Cited

OTHER PUBLICATIONS

Iwai et al., "Finger-Powered MicroDroplet Generator," The 16th International Solid-State Sensors, Actuators, and Microsystems Conference (Transducers 2011), Jun. 2011, pp. 230-233.
Unknown, "Enhanced Mobile Satellite Services (EMSS) Iridium," GlobalSecurity.org, Jul. 21, 2011, Retrieved from the Internet: http://www.globalsecurity.org/space/systems/iridium.htm.
Zahn et al., "Continuous on-Chip MicroPumping Through a MicroNeedle," The 14th International Conference on MicroElectroMechanical Systems (MEMS), Jan. 2001 pp. 503-506.

* cited by examiner

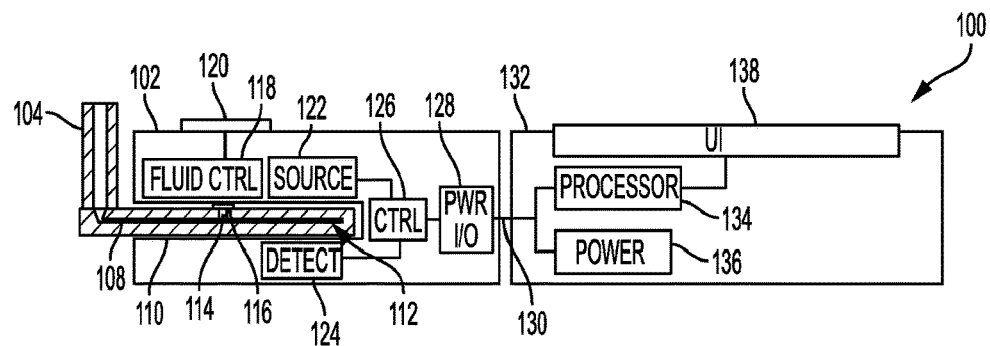
FIG. 1
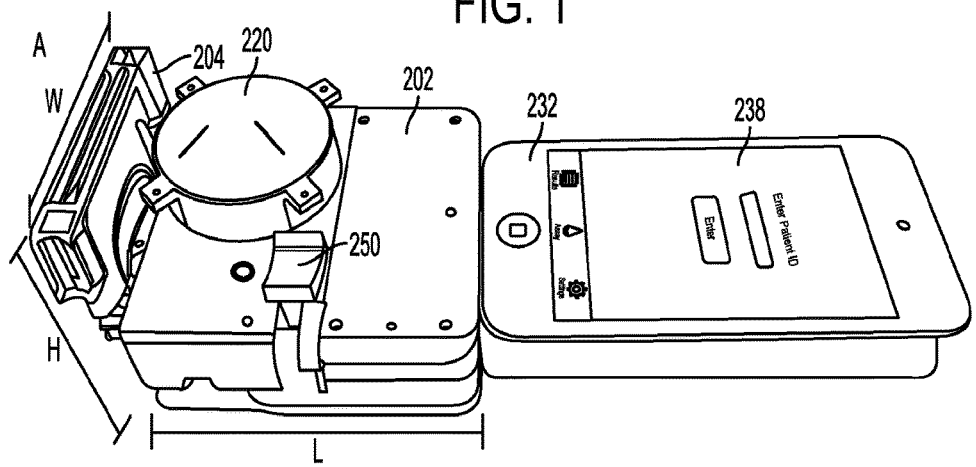
FIG. 2A
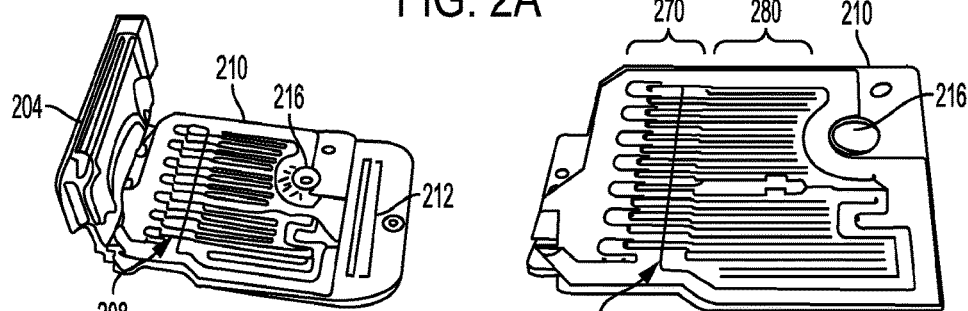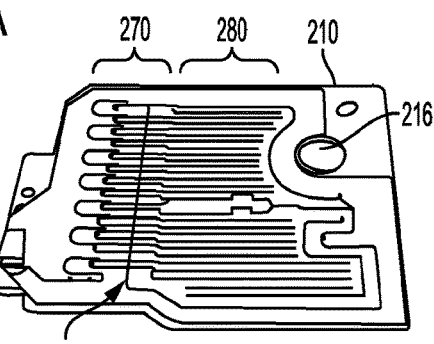
FIG. 2B  FIG. 2C
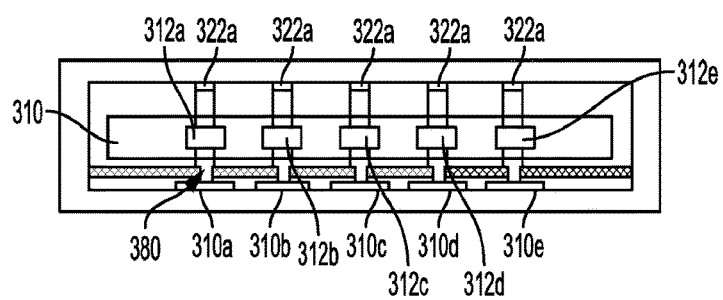
FIG. 3A

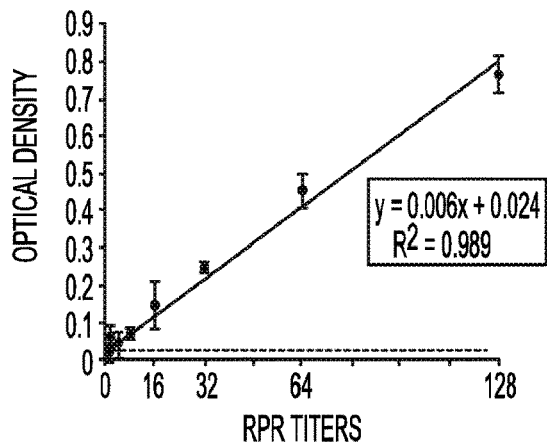
FIG. 17
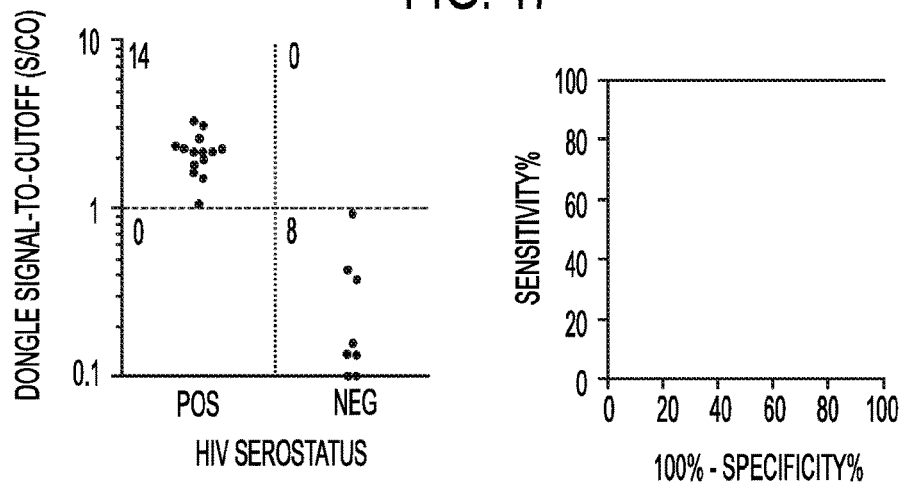
FIG. 18A
FIG. 18B
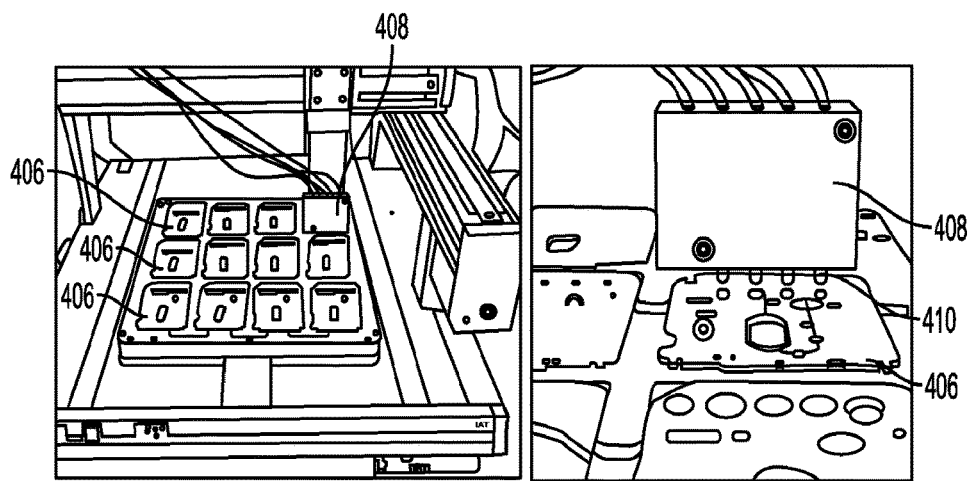
FIG. 19A
FIG. 19B

_US 10,444,232 B2_

DIAGNOSTIC DEVICES, SYSTEMS, AND METHODS

CROSS-REFERENCE TO RELATED APPLICATIONS

This application is a U.S. national stage filing under 35 U.S.C. § 371 of International Application No. PCT/US2015/045034 filed Aug. 13, 2015, the content of which is hereby incorporated by reference in its entirety, which claims the benefit of U.S. Provisional Application No. 62/036,987, filed Aug. 13, 2014, and U.S. Provisional Application No. 62/077,782, filed Nov. 10, 2014, both of which are hereby incorporated by reference herein their entireties.

STATEMENT REGARDING FEDERALLY SPONSORED RESEARCH

This invention was made with government support under AID-OAA-A-12-00007 awarded by United States Agency for International Development (USAID). The government has certain rights in the invention.

FIELD

The present disclosure relates generally to diagnostic systems, and, more particularly, to low-cost, handheld, extremely-low-power diagnostic devices, systems, and methods.

BACKGROUND

Diagnostic systems designed for ease of use and/or low cost may be desirable for field applications. For example, screening for low hemoglobin concentration, or anemia, is critical in antenatal care, as untreated anemia in pregnancy can lead to pre-term delivery, low birth weights, and increased risk of maternal and fetal deaths. Because the risk factors for anemia include pregnancy, micronutrient deficiencies, and infectious diseases, anemia is especially prevalent in pregnant women in developing countries. Existing methodologies for hemoglobin determination range from conductometric to microcytometery. In addition to measuring hemoglobin concentration, it is important for pregnant women to be screened for HIV infection. If diagnosed in a timely manner, both anemia and HIV can be effectively treated (e.g., with iron supplements and anti-retroviral drugs, respectively), allowing for dramatic improvements in outcomes for both mother and infant. The disclosed subject matter addresses the needs of this and other applications.

SUMMARY

Point-of-care diagnostics are an important and growing field of medical technologies. Being able to perform complex biological assays that interface with a smart-enabled device (such as, but not limited to, smartphones, cell phones, tablets, laptops, and other portable electronic devices) will allow these assays to become more even accessible. In resource-limited areas, such as in rural settings and developing countries, embodiments of the disclosed subject matter can enable complex biological assays to be performed by minimally-trained users, allowing for an overall increased level of health-care services.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIG. 1 shows a schematic diagram of features of a diagnostic device, according to one or more embodiments of the disclosed subject matter.

FIG. 2A shows a diagnostic device coupled to a smartphone, according to one or more embodiments of the disclosed subject matter.

FIG. 2B is an image of a two-layer disposable cassette with an antibody holder and reagent stored cassette, according to one or more embodiments of the disclosed subject matter.

FIG. 2C is an image of the reagent cassette for pre-stored wash and silver reagents for use by a smartphone dongle device, according to one or more embodiments of the disclosed subject matter.

FIG. 3A is a cross-sectional view of a detection region of a diagnostic device, according one or more embodiments of the disclosed subject matter.

FIG. 17 is a graph of optical density (OD) for nontrepnonemal syphilis quantitative assay performed by detecting anti-cardiolipin antibodies, according to one or more embodiments of the disclosed subject matter.

FIGS. 18A-18B show vertical scatter plot of silver absorbance for positive and negative HIV specimens and the receiver-operating characteristic (ROC) curve, respectively, according to one or more embodiments of the disclosed subject matter FIGS. 19A-19B show an overall image and a close-up image of an exemplary robot-assisted manufacturing setup for cassette preparation, according to one or more embodiments of the disclosed subject matter.

DESCRIPTION

Figure 3B:
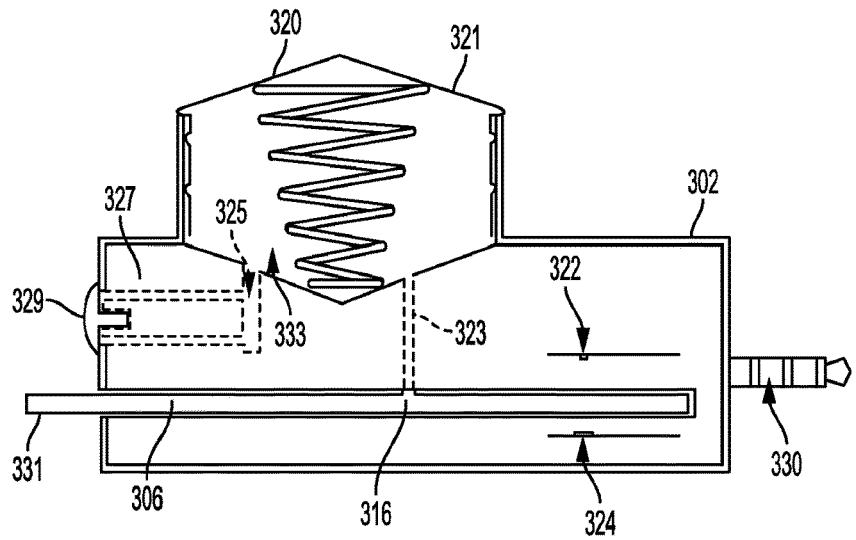
FIG. 3B shows another cross-sectional view of a diagnostic device, according to one or more embodiments of the disclosed subject matter.

In one or more embodiments of the disclosed subject matter, a diagnostic system 100 can include a diagnostic device 102 and a smart-enabled device 132, as illustrated in FIG. 1. An antibody holder 104 can hold antibodies for use in testing by the diagnostic device 102 and can be coupled to a reagent cassette 106. The reagent cassette 106 can include a channel network 108 including one or more microfluidic channels (e.g., channels having a height and/or width perpendicular to a direction of flow therethrough less than 1 mm). The reagent cassette 106 may further include one or more chemicals or reagents for performing a desired assay by the diagnostic device 102.

The reagent cassette 106 can be inserted into a slot or recess 110 of the diagnostic device 102 in order to perform the desired assay. Once inserted, an outlet 116 may align with a flow control portion 118 of the diagnostic device 102, for example, to allow pressure to drive fluid in the microfluidic network 108 of the cassette 106. For example, the fluid control portion 118 can be constructed to provide a negative-pressure to the outlet 116 to pull fluid through the microfluidic network 108. An O-ring 114 can act as a seal between a wall of the slot 110 and the outlet 116 of the cassette 106. The fluid control portion 118 can be actuated via actuator 120. For example, actuator 120 can be a button or rubber bulb that forms a negative pressure in the fluid control portion 118. The arrangement of the actuator 120 and the overall size of diagnostic device 102 may be such that a user can hold the diagnostic device 102 and actuate the actuator 120 using a single hand, while allowing access to controls via the user interface 138 of the smart-enabled device 132 via the same hand (e.g., using the thumb to depress actuator 120 and subsequently accessing controls with the thumb on a screen of the user interface 138) or via the other hand (e.g., using the thumb of a hand supporting the devices 102, 132 to depress actuator 120 while simultaneously or subsequently accessing controls on a screen of the user interface 138 with the same or the other hand). The position of the actuator 120 facing forward helps to reduce the risk of accidental actuation since the diagnostic device can readily be handled by the edges. I may be more likely for an actuator positioned out of view (while facing the display) to be pressed accidentally. Concomitantly, when actuation is desired, there may be minimal fumbling for the actuator 120 due to its conspicuous position while facing the display. The embodiments are not limited to front-facing actuator positioning.

Once inserted, the cassette 106 may have a detection region 112 (comprised of one or more detection zones) arranged so as to be interrogated by at least one source 122 and at least one detector 124. Although shown on opposite sides of the cassette 106, the arrangement of the source 122 and the detector 124 is exemplary only and other arrangements are also possible according to one or more contemplated embodiments. For example, the location of the source 122 and detector 124 can be switched or the source 122 and detector 124 may be located on a same side of the cassette. The source 122 and detector 124 may be used to analyze a substance in the detection zone 112 as part of the predetermined assay. For example, the source and detector may be configured to perform a spectroscopic analysis, a fluorescence analysis, a light absorption analysis, or any other analysis known in the art.

Power for the source 122 and detector 124 can be provided via the smart-enabled device 132, for example, by inserting a connector 130 into a corresponding receptacle of the smart-enabled device 132, or vice versa. For example, the connector 130 can be adapted to an existing receptacle of the smart-enabled device 132, such as an audio jack port or USB port. An onboard power source 136, such as a battery, can thus provide power to both the diagnostic device 102 and the smart-enabled device 132.

In addition, the diagnostic device 102 can be configured to convey data from the performed assay to the smart-enabled device 132 for further processing and/or display on user interface 138. In particular, the diagnostic device 102 can use the same connector 130 that it uses for power to transmit information between the diagnostic device 102, for example a control module 126 that receives signals from at least the detector 124 and generates data therefrom, and the smart-enabled device 132, for example a processor 134 that may have an application (i.e., app) or other software program installed thereon to control the smart-enabled device 132 and/or the diagnostic device 102.

Referring now to FIG. 2A, an example of an assembled diagnostic system including a diagnostic device 202 and a smartphone 232. The diagnostic device 202 (also referred to herein as the "mChip Dongle") can be low-cost and extremely-low-power. For example, the diagnostic device 202 can have a width (W) of 7 cm, a height (H) of 5 cm, and a length (L) of 7.5 cm. The device 202 can weigh, for example, 130 grams and have an overall size of, for example, 260 in$^3$ so as to fit in one hand of a user.

Figure 5:
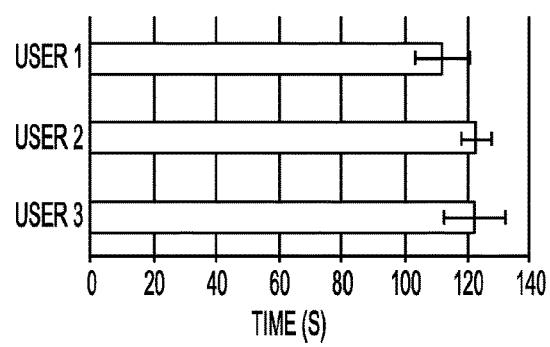
FIG. 5 shows reproducibility results of total flow time for six washes with different users of a diagnostic device, according to one or more embodiments of the disclosed subject matter.

A manual bulb-type actuator 220 can be arranged with respect to the user interface 238 of the smartphone 232 such that the user can operate the system single-handedly (e.g., using a thumb or a portion of the palm to actuate the bulb 220 and/or to interact with the user interface 238) or using two-hands. The cost of the diagnostic device 202 can be less than $100, for example, ~$63 (or less than $34, or even less depending on economies of scale). The test cassette 210/ antibody chamber 204 (FIGS. 2B-2C), which may be a one-use disposable item, may have a cost substantially less than that of the device 202, for example, ~$2. The cassette 210 may have microfluidic network 208 (as 108, supra) and an outlet 216 (as 116, supra). The system may be configured to provide a minimal number of user steps, for example, six, and be able to perform an assay relatively quickly, for example, in less than 15 minutes (for example, as illustrated by the results of FIG. 5).

Referring to FIG. 3A, a simplified cross-sectional view illustrates certain aspects of the detection zones 312 of the reagent cassette 306 and interrogation by the illumination sources 322 and photodetectors 310. The reagent cassette 306 can be inserted into the diagnostic device 202 such that each detection zone 312a-312e can be aligned with the optical path of a respective pair of light sources 322a-322e (e.g., individual LEDs) and photodetectors 310a-310e (e.g., photodiodes). Light from each light source 322 thus interacts with the respective sample in detection zone 312 and causes changes in the light incident on the respective photodiode 310, for example, reduction in the light intensity due to the presence of opaque particles as a result of an immunoassay or reduction in the light intensity due to absorption by a substance (e.g. hemoglobin) at the detection zone 312. Pinholes apertures 380 can be provided in the optical path between each detection zone 312 and the respective photodiode 310a to reduce potential crosstalk or background noise.

Referring to FIG. 3B, a simplified cross-sectional view illustrates certain aspects of the diagnostic device according to one or more embodiments of the disclosed subject matter. The diagnostic dongle 302 can be built to interface with a microfluidic chip 306 (i.e., reagent cassette). The microfluidic chip 306 can have an outlet 316 that is aligned and sealed by a rubber O-ring (not shown) with a channel 323 fluidically connecting to the negative-pressure chamber 333. The negative-pressure chamber 333 is a fully enclosed chamber with a depressible top 320 (e.g., rubber bulb) and a spring 321 therein. The negative-pressure chamber 333 connects to the chamber outlet 316 and to an outlet 327 to atmosphere, which outlet 327 may be sealed with a one-way valve 329 (oriented to allow flow out of the chamber 333, but not into the chamber 333).

Note that, as the term "dongle" is used in the instant specification, it is intended to refer to a device that can be selectively attached to a separate component in order to share features of the separate component in order to achieve a predefined function in the combination. Thus, neither separate component (e.g., smart phone) nor the dongle can perform the target function without the other. In embodiments, a dongle is a connectable accessory. In further embodiments, the dongle may function on its own, but its functionality can be enhanced by attachment to the separate component. The term dongle does not identify a master-slave relationship in all embodiments. Further, it does not connote a lack of functionality independent of the separate component to which it is connectable.

The size of the channel 323 connecting to the outlet 316 and the size of the outlet channel 325 to atmospheric outlet 327 can be such that air preferentially flows out one way valve 329 rather than into the microfluidic network upon depressing bulb 320. Thus, as illustrated schematically in FIG. 4A, when the user presses the bulb 320 downward, air exits to atmosphere via the one-way valve 329, since there is too much resistance for significant air to flow into the microfluidic outlet 316. When the user releases the bulb 320, it expands with the aid of the spring 321, as illustrated schematically in FIG. 4B. The one-way valve 329 prevents air from the atmosphere from re-entering the chamber 333 via the one-way valve outlet 327. Pressure in the chamber 333, after release, can be a fraction of atmospheric pressure (e.g., 1 atm) and can be negative relative to atmospheric conditions, or $P_{chamber} = V_{compressed}/V_{chamber}$, where $V_{compressed}$ is the volume of the chamber 333 in the compressed state, and $V_{chamber}$ is the volume of the chamber 333 in the fully expanded state. Similar power-free mechanisms to generate a negative pressure chamber at the time of assay start (as opposed to a prepackaged negative pressure chamber) can also be used according to one or more contemplated embodiments.

Figure 6:
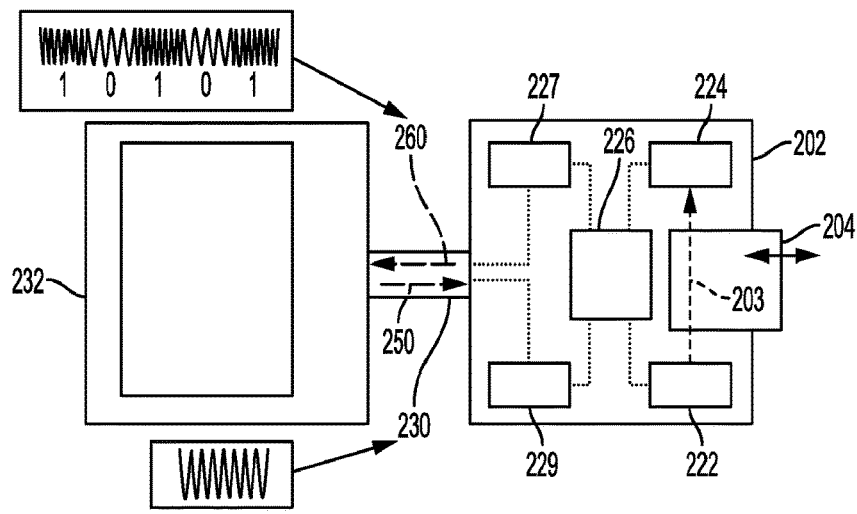
FIG. 6 illustrates aspects of the power and data transmission between a smartphone and the diagnostic device, according to one or more embodiments of the disclosed subject matter.

In one or more embodiments of the disclosed subject matter, a connection between the diagnostic device 202 and the smart-enabled device 232 can power the diagnostic device 202 and/or smaret-enagled device 232 and data transmission between them. For example, as illustrated in FIG. 6, the audio jack 230 of a smartphone 232 can be used for both power delivery 250 and signal transmission 260. For example, a 19 kHz audio signal can be sent from the smartphone 232 to the diagnostic device 202 via one of the audio channels 250 (e.g., through the left audio channel using only 0.22 mWh). The signal can be converted to a constant DC power (e.g., 3.0V DC) using a voltage rectifying circuit 229 and used to power the device 202. As a result, the diagnostic device 202 can be provided without any internal battery and may use only the power delivered by the audio signal.

A control unit 226, (e.g., a microcontroller, such as controller 126 in FIG. 1) can send the information regarding the assay results or other operation of the diagnostic device through the audio jack 230 via frequency-shift keying (FSK). In FSK, the decimal integer is converted into binary and each digit is sent as either 1600 Hz (1) or 800 Hz (0) at a rate of 1 bps. For example, a signal from the photodiode 224 indicative of light 203 from 222 passing through the detection zone of cassette 204 can be converted by data conversion module 227 into 16-bit binary numbers, which are then sent via FSK at a 1 bps baud rate. The smartphone 232 can include an app that decodes the received audio signals 260, for example, by converting back to decimal numbers with little or no error rates.

Although the discussion above focuses on the use of the audio jack 230 of the smartphone 232 to provide data transmission and electrical power to the diagnostic device 202, other connections of the smart-enabled device 232 can be used in a similar manner according to one or more contemplated embodiments. For example, power and/or data transmission connections can be provided by an Apple lightning cable, a microUSB connection, or a USB connection. Alternatively or additionally, data transmission between the diagnostic device and the smart-enabled device can be accomplished via wireless communications, such as, but not limited to, Wi-Fi, near-field communication (NFC), or low-energy Bluetooth. Such configurations may employ a small on-board battery for powering the diagnostic device.

In one or more embodiments of the disclosed subject matter, a diagnostic device can be used for the diagnosis of human immunodeficiency virus (HIV) or syphilis via measurement of reduction in light received at the photodetector on the microfluidic chip. Alternatively or additionally, the diagnostic device can be adapted for any test that can be performed via immunoassay or colorimetric detection. Alternatively or additionally, the diagnostic device can be further adapted for electrochemical detection, for example, by incorporating a small heater and configuring for nucleic acid detection. Such configurations may also employ a small on-board battery for the diagnostic device.

In one or more embodiments of the disclosed subject matter, a full laboratory-quality immunoassay can be run on a smartphone accessory. This low-cost dongle can replicate all (or least many) mechanical, optical, and electronic functions of lab-based enzyme-linked immunosorbent assay (ELISA) without stored energy. Rather, all (or least most or at least a majority) of the power can be drawn from a smartphone.

Embodiments of the disclosed subject matter may be relatively low cost as compared to traditional bench top assay systems. For example, using commercially available electronic components with an injection-moldable case, the dongle device can have a manufacturing cost in the tens of dollars (e.g., $34 or less), in comparison to typical ELISA equipment that costs on the order of tens of thousands of dollars (e.g., $18,000). For example, this "dongle" measures 7 cm×7.5 cm×5 cm, and weighs 130 grams. Thus, the dongle can be small and light enough to fit in one hand. The dongle can run assays on disposable plastic cassettes with pre-loaded reagents where disease-specific detection zones will provide an objective read-out, similar to an ELISA microplate assay but with gold nanoparticles and silver ions performing the amplification step instead of enzymes and substrate.

For example, the dongle device can be configured to perform at least three separate assays at the same time. For example, a triplex test with HIV, treponemal syphilis, and non-treponemal syphilis results can potentially better identify active syphilis infections since treponmemal syphilis antibody level remains high for life. IgM can be added as a secondary antibody for detecting early-stage syphilis.

As described above, the dongle can have features that help achieve low power consumption. For example, a power-consuming electrical pump can be avoided by using a "one-push vacuum", where a user mechanically activates a negative-pressure chamber in order to move a sequence of reagents stored within a cassette. The simple vacuum chamber can be created with a rubber bulb, with one port connected to the assay cassette outlet, and one port to a silicone one-way valve. When the bulb is depressed, air exits out the one-way valve, and a spring aids the bulb in re-expansion, creating a negative pressure within the chamber that pulls liquids through the cassette. As illustrated in FIG. 5, the flow rate can be relatively consistent over several users. In FIG. 5, three different operators pushed the rubber bulb to activate negative-pressure drive flow. Flow times are shown for 6 washes: two 1.3 μL washes of 0.05% polyoxy-ethylene-sorbitan monopalmitate (Tween) in phosphate buffered saline (PBS) and four 1.3 μL washes of DI water. Error bars show one standard deviation (n=3) and the black bar indicates no significant difference (p>0.05) between the three users.

Figure 9:
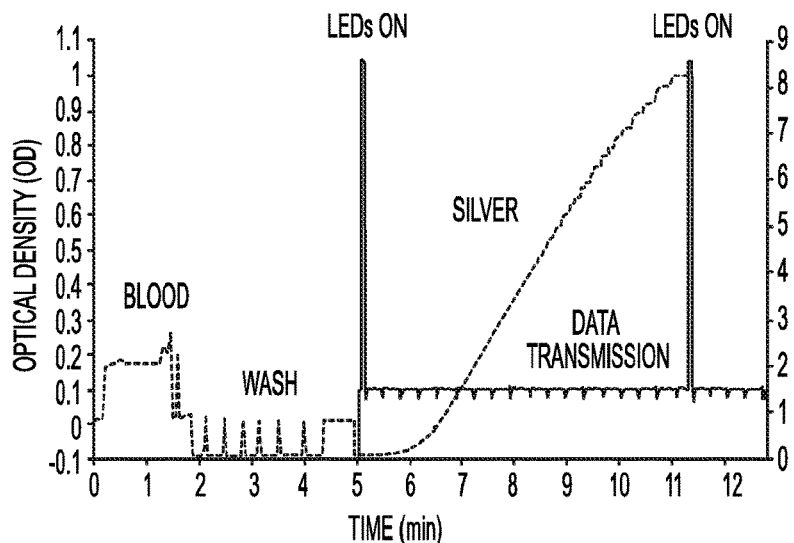
FIG. 9 is a graph illustrating operation of the smartphone dongle device, according to one or more embodiments of the disclosed subject matter, over the course of an assay.

Other components in the dongle, including robust and low-cost LEDs, photodetectors, and a microcontroller, consume very low power. The dongle measures the optical density (i.e., absorbance) of silver enhancement on each assay. The dongle can be designed such that power is only consumed during optical density readings (e.g., on the order of 8.5 mW) and information transfer back to the smartphone (e.g., on the order of 1.5 mW), as illustrated by FIG. 9, where the power consumption (black, axis on right) and optical density in the HIV zone (red, axis on left) over the course of the 12.5 minute assay is shown. High optical density is observed while whole blood flows through the zones, with low optical density during washes. Air gaps are seen as blips of mildly higher absorbance. At minute 5, silver starts to flow over the HIV zone and optical density increases as silver develops. The dongle is not powered until silver has entered the zones and optical density readings take place (starting at minute 5). The power is mainly at baseline of 1.49 mW with the exception of two 4 second periods when LEDs turn on and optical density readings are taken.

Thus, no power (or at least a minimal amount of power) is consumed by the dongle while sample and washes are flowing. For example, over the course of the 15-minute assay, the dongle has an average power consumption of 1.6 mW. By comparison, an iPhone 4 uses 751 mW on a 3G network and 17.5 mW on standby mode, and a laser pointer uses about 5 mW. With such low power consumption by the dongle, the need for an on-board power supply (e.g., a battery) can be avoided, thereby further reducing the cost and/or weight of the dongle. In addition, the audio jack of the smartphone can be used for transmitting power and for data transmission. Over time, the audio jack connection (3.5 mm, 4 lead) has remained relatively ubiquitous and standardized, which allows embodiments of the disclosed dongle to be compatible with the growing variety of mobile phones and tablets. Thus, the dongle can have no internal battery and can use only the electrical power delivered by the audio signal.

In embodiments, a diagnostic device may be configured to perform an assay on a sample in a microfluidic channel and to apply a negative pressure to the microfluidic channel contemporaneously with, or in response to, a manual actuation such as activation of a control or pressing of a vacuum actuator such as the bulb. During the diagnostic assay the diagnostic device may perform sample flow and washes in said microfluidic channel at first times and perform optical density readings and generates data responsively to the optical density readings at second intervals of the diagnostic assay. The diagnostic device may have a connector for interfacing with a smart-enabled device. The diagnostic device may be configured to draw power and transmit data via said connector. The first rate may be about 1.6 mW and the second rate may be about 8.5 mW. Variations in the power consumption may occur over the first and second intervals and the magnitudes may be different from these particular examples. For example, but by using manual vacuum generation and targeted design for low power consumption including restricting power use to time when it is essential (for example illumination, detection, and data generation), according to various implementations, the diagnostic device may draw power at a first rate during said first intervals and at a second rate during said second intervals. The second rate may be at least 4 times greater than the first rate. The first rate may be less than 3 mW. The first rate may be less than 2 mW. The first rate is variable and average between 5 and 15 mW.

Figure 10:
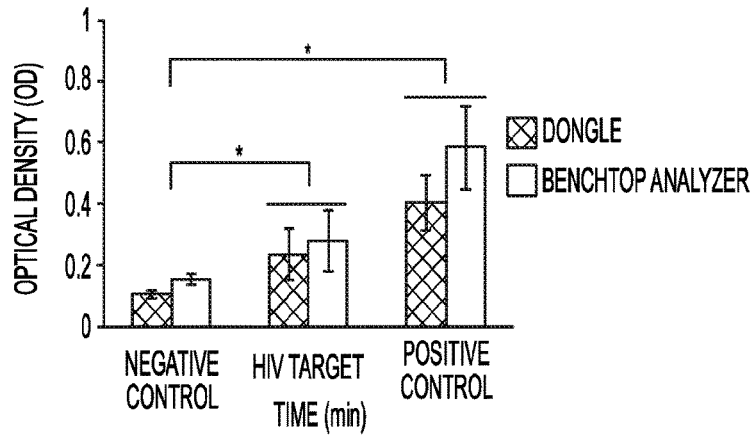
FIG. 10 is a graph of optical density (OD) signal measurements for various detection zones obtained by a benchtop analyzer and the dongle device, according to one or more embodiments of the disclosed subject matter.

The power harvested from the audio jack is stable and sufficient for reliable optical density measurements compared to a benchtop analyzer. For example, FIG. 10 shows a comparison of optical density (OD) signal measurements for various detection zones obtained by the dongle and benchtop analyzer. An HIV positive whole blood sample was run in triplicate, where measurements were taken with the iPod powered dongle and benchtop analyzer reading the same cassette. Optical density values were calculated on three detection zones for analysis: negative control, HIV target, and positive control to show a range of signal readings. Average values (n=3) for each detection zone taken by their respective device were plotted, and student two-tailed t-test was used to calculate statistical significance ($p<0.05$ considered significant). Errors bars show one standard deviation (n=3). Overhead black bars indicate no statistically significant ($p>0.05$) difference in signals obtained by the dongle and benchtop analyzer. Asterisks indicate statistically significant ($p<0.05$) difference in signals between detection zones. For the target and positive control zones, there was no significant difference in OD measurements taken by the dongle and benchtop analyzer. For the negative control zone, the benchtop analyzer and dongle showed differences ($p=0.03$). The disparity in signals at the low end of the spectrum was not found to be clinically relevant, since the dongle maintained statistically significant separation of OD readings between the negative control and target or positive control zones.

A control module in the dongle, for example, a microcontroller and/or a conversion module of a control unit, can be programmed to perform, for example, frequency-shift keying (FSK) by converting a decimal integer into binary. Each bit can be sent as a high-frequency (1632 Hz, or "1") or low-frequency (816 Hz, or "0") signal. The microcontroller can transmit the photodiode readings through the audio jack and back to the phone, for example, as illustrated schematically in FIG. 6 and referenced above. Although implementations described herein focus on fidelity of the transmitted signal, increased speeds with potential reduced fidelity for the signal transmission are also possible according to one or more contemplated embodiments.

Figure 7:
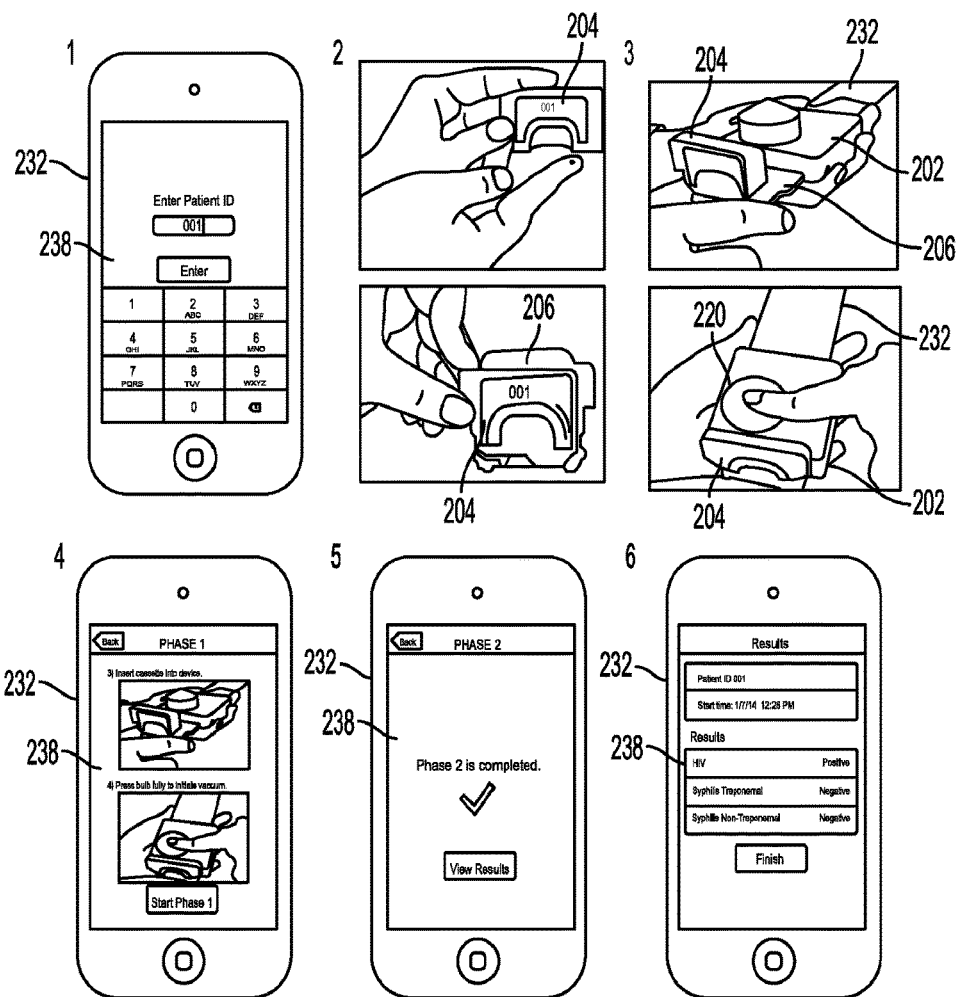
FIG. 7 is a step-by-step illustration of using a smartphone and dongle device to perform a test, according to one or more embodiments of the disclosed subject matter.

To test the accuracy of the signal, a microcontroller was programmed to send a pattern of alternating "1" and "0", or high frequency and low frequency signals. An accuracy of 100% for 12,160 bits tested was observed. A custom smartphone application (app) on the phone converted the signals to absorbance units, which can be reported to be "positive" or "negative" when compared to a cut-off value. The app also presented a user-friendly interface to aid the user through each test, step-by-step pictorial directions, built-in timers to alert the user to next steps, and records of test results for later review (as illustrated in FIG. 7).

Figure 11:
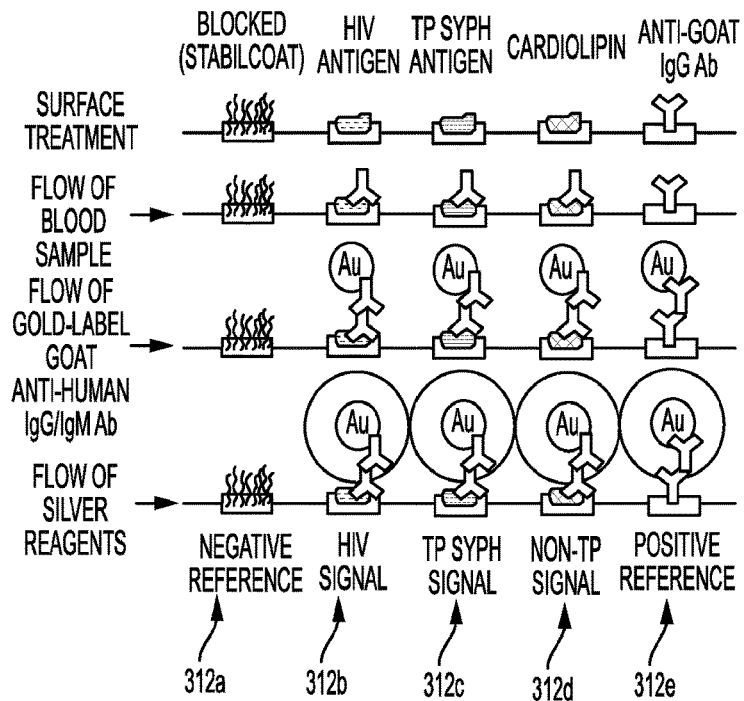
FIG. 11 is a schematic diagram of a multiplex immunoassay and biochemical reactions at each step of reagents flowing through the microfluidic channel in a smartphone dongle system, according to one or more embodiments of the disclosed subject matter.

In one or more embodiments of the disclosed subject matter, the number of detection zones may be at least two, and in some embodiments, at least 5. For example, the disposable microfluidic cassette can have five detection zones, for detecting HIV, treponemal syphilis, and non-treponemal syphilis antibodies simultaneously with internal negative and positive control. FIG. 11 illustrates a multiplex immunoassay on the dongle device and the biochemical reactions at each step of reagents flowing through the microfluidic channel Five zones 312a-312e are individually treated with proteins: Stabilcoat for internal negative reference at zone 312a, HIV antigen for capturing anti-HIV antibodies (Ab) at zone 312b, treponemal syphilis (TP syph) antigen for capturing anti-treponemal antibodies at zone 312c, cardiolipin for capturing anti-cardiolipin antibody (non-treponemal biomarker) at zone 312d, and rabbit anti-goat antibody for capturing gold (Au)-labeled goat antibodies for internal positive reference at zone 312e. The fourth zone 312d for non-treponemal syphilis is coated with Poly-Lysine prior to the cardiolipin attachment. Whole blood samples can be loaded in the antibody holders 204 (as shown in FIG. 2B and FIG. 6) or into the inlet of the microfluidic network of the reagent cassette 206. Pre-loaded washes on reagent cassette 206 can be flowed through the antibody holders 204 to resolubilize lyophilized Au-labeled IgG and IgM antibodies contained therein, followed by the flow of silver reagents within reagent cassette 206.

Figure 12A:
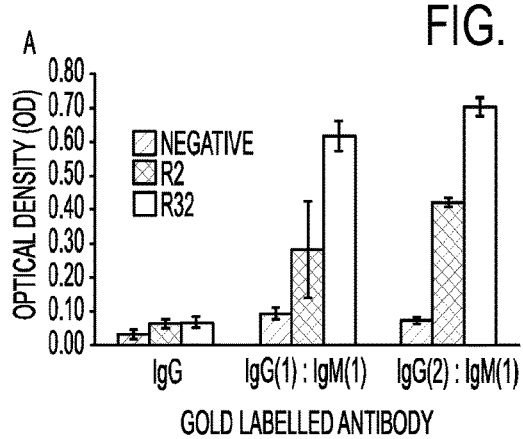
FIG. 12A is a graph comparing optical density (OD) signal measurement obtained by gold-labeled anti-hIgG, gold-labeled anti-hIgG:gold-labeled anti-hIgM at 1:1 ratio, and gold-labeled anti-hIgG:gold-labeled anti-hIgM at 2:1 ratio as detection antibodies for negative, weak positive non-treponemal syphilis (RPR titer 1:2), and strong positive non-treponemal syphilis (RPR titer 1:32) plasma samples, according to one or more embodiments of the disclosed subject matter.
Figure 12B:
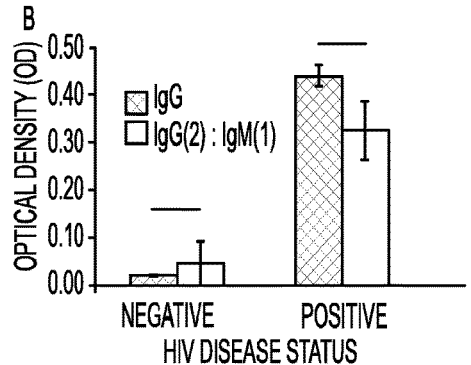
FIG. 12B is a graph comparing optical density (OD) signal measurements obtained by additional gold-labeled anti-hIgM on HIV detection from HIV negative and positive plasma samples, according to one or more embodiments of the disclosed subject matter.

In one or more embodiments of the disclosed subject matter, gold-labeled IgM antibodies can be added to the assay. FIGS. 12A-12B show results for gold-labeled anti-human IgG and IgM for syphilis and HIV detection. In particular, FIG. 12A shows a comparison of optical density (OD) signal measurements obtained by gold-labeled anti-hIgG, gold-labeled anti-hIgG: gold-labeled anti-hIgM at 1:1 ratio, and gold-labeled anti-hIgG:gold-labeled anti-hIgM at 2:1 ratio as detection antibodies for negative, weak positive non-treponemal syphilis (RPR titer 1:2), and strong positive non-treponemal syphilis (RPR titer 1:32) plasma samples. FIG. 12B shows the effect of additional gold-labeled anti-hIgM on HIV detection from HIV negative and positive plasma samples. Errors bars show one standard deviation (n=2). Overhead black bars indicate no statistically significant (p>0.05) difference in signals obtained by adding anti-hIgM antibodies.

Figure 13:
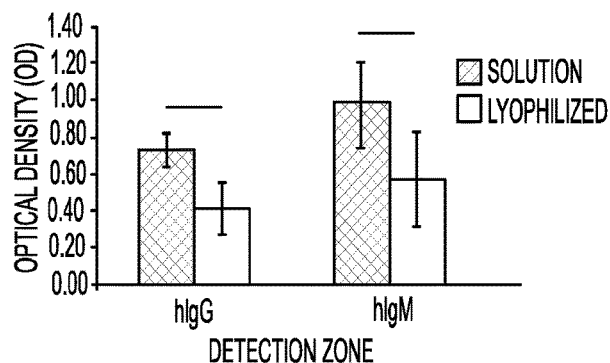
FIG. 13 is a graph comparing lyophilized gold-labeled anti-hIgG/anti-hIgM antibodies in a plastic antibody holder and gold-labeled anti-hIgG/anti-hIgM antibodies in buffer as detection antibodies using optical density (OD) signal measurements of microfluidic detection zones functionalized with human IgG and human IgM antibodies, according to one or more embodiments of the disclosed subject matter.

In one or more embodiments of the disclosed subject matter, to improve long term stability in shipping and storage, gold-conjugated secondary antibodies can be lyophilized inside the antibody holder 204, along with a stabilizer and anticoagulant. Lyophilization can enable the secondary antibodies to be stable for over 6 months at room temperature and can show comparable performance as gold-conjugated antibodies freshly diluted in buffer. For example, FIG. 13 compares lyophilized gold-labeled anti-hIgG/anti-hIgM antibodies in a plastic antibody holder 204 stored at 4° C. for 5 months and freshly prepared gold-labeled anti-hIgG/anti-hIgM antibodies in buffer as detection antibodies using optical density (OD) signal measurements of microfluidic detection zones functionalized with human IgG and human IgM antibodies. Errors bars show one standard deviation (n=2). Overhead black bars indicate no statistically significant (p>0.05) difference in signals. Alternatively or additionally, the antibody holder can be packed in an individual moisture bather bag prior shipment to an end user.

Figure 14A:
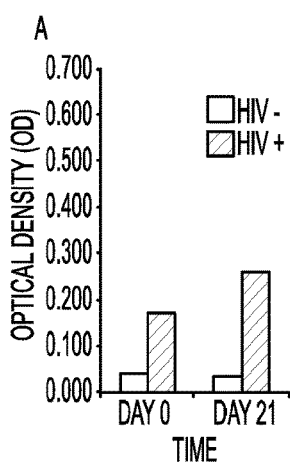
FIGS. 14A-14C are graphs of optical density (OD) signal measurements illustrating stability over time of functionalized protein on a surface at 60° C. for HIV 1/2 antigens, treponemal syphilis antigen, and cardiolipin, respectively, according to one or more embodiments of the disclosed subject matter.
Figure 14B:
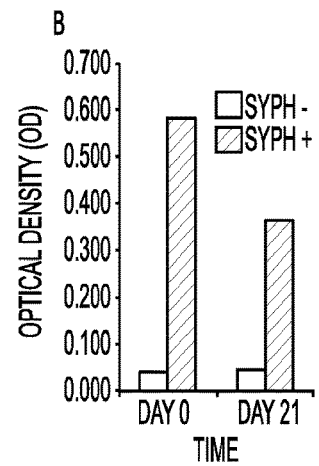
Figure 14C:
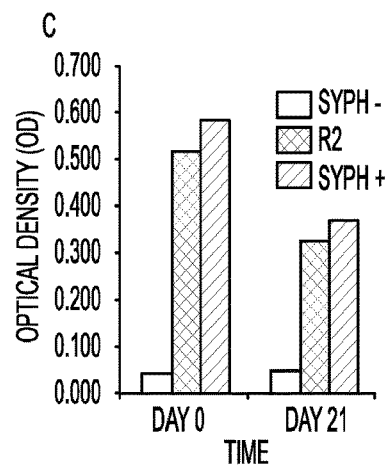
Figure 15A:
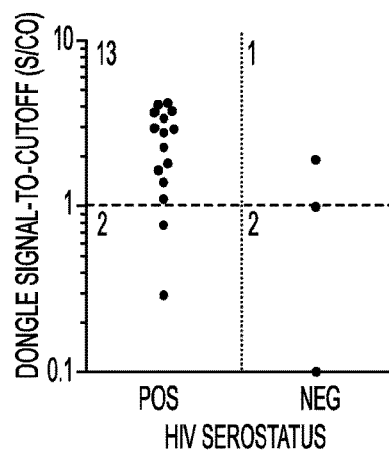
FIGS. 15A-15B are graphs of sensitivity and specificity, respectively, of a smartphone dongle HIV assay using undiluted whole blood samples, as compared to HIV ELISA, for cassettes functionalized with HIV chimeric antigen concentrations of 2 µg/mL, according to one or more embodiments of the disclosed subject matter.
Figure 15B:
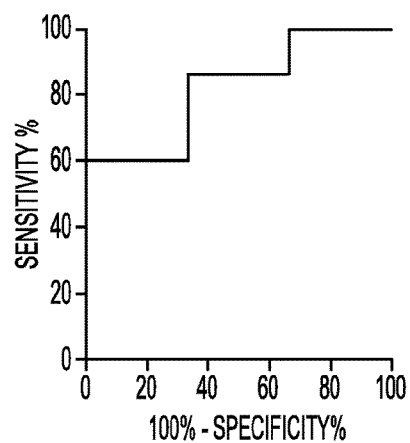

In one or more embodiments of the disclosed subject matter, the test cassettes 206 can be prepared prior to shipment using a stabilizing agent during physisorption of capture proteins. FIGS. 14A-14C illustrate the stability over time of the functionalized protein on a surface at 60° C. for HIV 1/2 antigens (FIG. 14A), treponemal syphilis antigen (FIG. 14B), and cardiolipin (FIG. 14C). Cassettes were prepared using StabilCoat Immunoassay Stabilizer® (Surmodics) and stored in an oven at 60° C. for the accelerated stability test. The preliminary stability test in the lab has shown a stable assay cassette for up to 3 weeks at 60° C. which is equivalent to 28 weeks at room temperature (25° C.) from Arrhenius equation. Accordingly, the protein may retain its original function over an extended period of time.

In one or more embodiments, the reagent cassette can be pre-loaded with wash buffers and silver reagents, for example, within a day or on a same day as testing. As shown in FIG. 2C, the reagent cassette can have pre-stored reagents needed for the assay. The cassette can have two main parts for on-board reagent storage: washes 270 and silver reagents 280. Each day prior to testing, reagents were loaded by hand into the reagent cassette to mimic prepackaged reagents. However, a robotic device 408 using one or more pipette tips 410, for example, as illustrated in FIGS. 19A-19B, can be used for robot-assisted loading of reagent cassettes 406, which may allow high-throughput cassette preparation prior to shipment to an end user. Such reagents can be stable for over 6 months at room temperature. Wash plugs may stay separated even after airborne shipping.

FIG. 7 provides a step-by-step illustration of how a user performs a test. For example, at (1) the user starts the application on smartphone 232 and enters patient ID number on the user interface 238. At (2), the user draws ~1-2 µL of whole blood in an antibody holder 204 (or into cassette 206) and inserts the antibody holder 204 into a microfluidic cassette 206. At (3), the user inserts the cassette 206 into dongle device 202 and presses the bulb 220 fully to initiate vacuum. At (4), the smartphone 232 running the app displays step-by-step instructions for the user to follow as well as remaining assay time.

After 5 minutes, sample, gold-labeled antibodies, and washes will have passed through the chip, and the user is prompted to slide a toggle (e.g., toggle 250) to close a venting port, to thereby initiate flow of silver reagents. To prevent exposure of chemicals to the user, sample and reagents are contained in a membrane filter within the cassette 206, and the antibody holder 204 cannot be detached from the cassette 206 once connected to the cassette 206. Optical density readings are taken before and after silver development, and at the end of the assay (15 min) results for all markers are available and clearly displayed on the app interface 238.

At (5), after completing the assay, the user selects "View Results" on the user interface 238 to display test results. For example, another passcode could be added at this step for extra security and privacy. At (6), the smartphone screen 238 displays results for each disease marker. The user can then click the "Finish" button to prompt back to the first screen for the next test. Optionally or additionally, the smartphone can transmit test results via cloud or a short message to a pre-designated email address, phone number, and/or website.

Figure 16A:
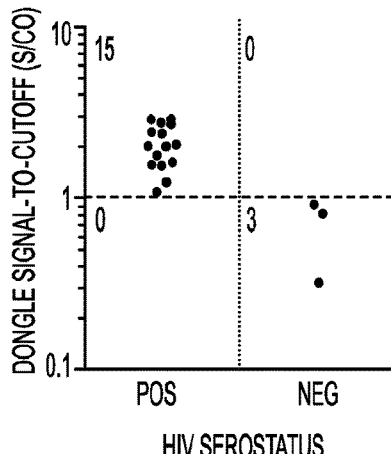
FIGS. 16A-16B are graphs of sensitivity and specificity, respectively, of a smartphone dongle HIV assay using undiluted whole blood samples, as compared to HIV ELISA, for cassettes functionalized with HIV chimeric antigen concentrations of 10 µg/mL, according to one or more embodiments of the disclosed subject matter.
Figure 16B:
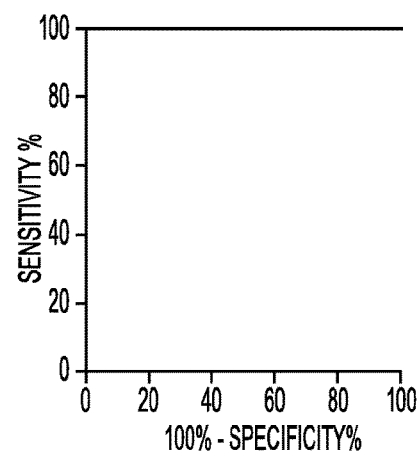

FIGS. 15A-16B shows sensitivity and specificity of smartphone dongle HIV assay using undiluted whole blood samples, compared to HIV ELISA for cassettes functionalized with HIV chimeric antigen concentrations of either 2 µg/mL (FIG. 15A-15B) or 10 µg/mL (FIG. 16A-16B). Signal performance was compared after testing with 18 whole blood samples, where cassettes spotted with the 10 µg/mL antigen spotting concentration yielded 100% sensitivity (CI, 78.20-100) and specificity (CI, 29.24-100), compared to those spotted with 2 µg/mL, which yielded 86.67% sensitivity (CI, 59.94-98.34) and 33.33% specificity (CI, 0.84-90.57). Cut-off values to determine if sample is reactive or non-reactive for each marker were selected by using receiver operating characteristic (ROC) curves. While a final product will offer preset cut-off values, in this development work, cut-off values were identified retrospective to data collection that maximize sensitivity (minimize false negatives) since the test is targeted towards screening applications. The ROC curves show the performance of the test across the entire range of possible cut-off values, with AUC (area under curves) reported for each test. Cut-off values for internal negative and positive controls were also applied to verify validity of test results. No test runs were excluded based on these criteria. An indeterminate range (e.g. if OD is within ±10-20% of cut-off) can be implemented for future tests, and indicate the user needs to rerun the test. The test results for detection of each marker are compared with the gold standards of lab-based HIV ELISA, syphilis TPHA, and syphilis RPR, and are presented in terms of signal-to-cutoff of each target relative to its reference test displayed as vertical scatter plots and ROC curves.

Figure 8:
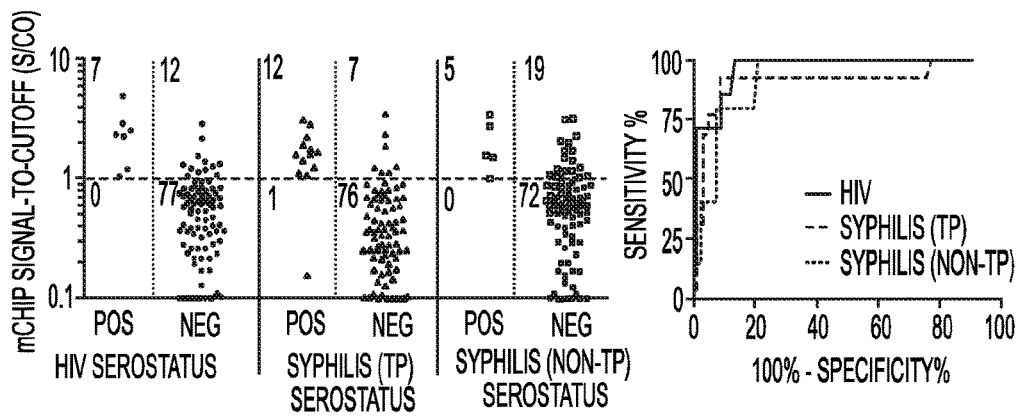
FIG. 8 shows a scatter plot (left) of dongle device signal-to-cutoff ratios (S/Co) for HIV, treponemal syphilis, and non-treponemal syphilis positive (Pos) and negative (Neg) samples using fingerprick whole blood and a graph (right) of receiver operating characteristic (ROC) curves for each disease marker.

FIG. 8 shows the results of dongle testing using clinical specimens. The left graph is a vertical scatter plot of the dongle device signal-to-cutoff ratios (S/Co) for HIV, treponemal syphilis and non-treponemal syphilis positive (Pos) and negative (Neg) samples using fingerprick whole blood compared to the gold standard of tests (i.e., HIV ELISA, TPHA, and RPR). The graph on the right shows a receiver operating characteristic (ROC) curve for each disease marker with the area under the curve (AUC) of 0.96 for HIV, 0.90 for treponemal syphilis, and 0.92 for non-treponemal syphilis. The detection of HIV antibodies had a sensitivity of 100% (95% CI: 59-100%) and specificity of 87% (95% CI: 78-93%). Sensitivity for detection of treponemal antibodies was 92% (95% CI: 64-100%) with specificity of 92% (95% CI: 83-97%). Sensitivity for detection of anti-cardiolipin antibodies was 100% (95% CI: 48-100%) with specificity of 79% (95% CI: 69-87%). The performances of these tests were comparable to those of current commercial rapid tests on whole blood (fingerprick or venipuncture) performed by trained staff in regular clinical settings: 1) HIV antibody tests (Clearview COMPLETE, Clearview STAT-PAK, OraQuick Advance, and Uni-Gold Recombigen): 97-100% sensitivity and ~100% specificity; 2) Determine HIV-1/2 showed lower specificity (85.2%) in one field evaluation; 3) Treponemal syphilis antibody tests (Determine, SD Bioline, Syphicheck, VisiTect, and Chembio): 64-96% sensitivity and 97-99% specificity; and 4) Non-treponemal syphilis antibody test (Chembio): 85% sensitivity and 96% specificity.

Embodiments of the disclosed dongle device and system can enable new capabilities for users ranging from health care providers to consumers. For example, for healthcare workers (HCWs), the dongle enables an ELISA-quality non-treponemal syphilis test to be performed at the point of care (POC). The dual-syphilis dongle allows HCWs to follow guidelines that recommend, in cases of positive non-treponemal but negative treponemal results, that no treatment is provided. Moreover, the addition of a POC non-treponemal syphilis test allows differentiation between active infections and past infections, which may be particularly valuable in endemic areas. In cases of positive treponemal and negative non-treponemal results, the dongle would enable HCWs to follow best practice guidelines that recommend for that a patient is treated only if he or she reports no previous infection or symptoms or history consistent with new infection.

Performing three individual tests using commercially available tests can cost up to $8.50 USD for the test kits ($0.80-$5 per test for HIV rapid test, $1-$3 for treponemal syphilis rapid test, and $0.50 for RPR). In contrast, material and reagents costs per test for the disclosed dongle triplex test are on the order of $1.44 USD, leaving room for a significantly lower anticipated market price for a combined test compared to existing separate tests, which also require separate finger pricks for each test.

Embodiments of the disclosed dongle device and system can detect IgM in addition to IgG antibodies, thereby enabling early detection of syphilis as anti-treponemal IgM antibodies appear earlier than anti-treponemal IgG by two weeks. The disclosed dongle platform has the flexibility of using labeled IgG/IgM for all disease markers compared to tests that use labeled antigens specific to each disease.

Additionally or alternatively, embodiments of the disclosed dongle device and system can be used for monitoring disease progression. For example, following treatment, a four-fold reduction in antibody titer is an indicator of successful treatment. As illustrated in FIG. 17, the dongle shows a strong correlation of optical density against a serial dilution of a strongly RPR positive syphilis sample (R2=98.9%). While several commercial readers are available to measure results of a lateral flow strip and provide quantitative readout, it can be difficult to reliably adjust for positioning, illumination accuracy, and dynamic range and hence influence accurate quantitation. Typically, precise liquid handling and metering is challenging when an untrained user executes the test, which can result in test errors. By contrast, the simple-to-use dongle can reproduce a full ELISA trace. The system further uses precise injection molded cassettes, pre-loaded reagents, highly optimized optics, and exact alignment that can offer a rapid and sensitive quantitation while reducing user variability.

Embodiments of the disclosed dongle device and system can utilize hardware that exhibits characteristics similar to familiar consumer electronics devices, e.g., low power (using a power-free, continuous-flow vacuum and requiring no separate charging of power), durable components (using LEDs and photodetectors), portability and low cost (e.g., less than a pair of headphones). The disposable cassettes can be robustly manufactured (e.g., with a robotic arm 408 as fluid dispenser 410 that can spot and block 12 cassettes 406 in two minutes) and pre-coated with proteins with stable reagents before shipping to the use location. The LEDs 322 and photodiodes 310 can be precisely aligned with the testing zones 312, with a set of 1 mm pinholes 380 made of 1 mm thick black Delrin above each of the photodiodes 310 to minimize noise from ambient light.

The housing for the dongle 302 can be formed of a polymer, for example, a polymer that has been 3-D printed, injection molded, hot embossed, or subjected to any other forming/machining technique. The one-way valve 329 and connection to microfluidic outlet 316 can be sealed with silicone rubber O-rings. A cylinder in the dongle housing 320 can be designed to fit tightly with a depressible covering 320 (e.g., a rubber bulb from a 140-mL syringe) with a conical spring 321 inside to aid re-expansion.

Figure 20A:
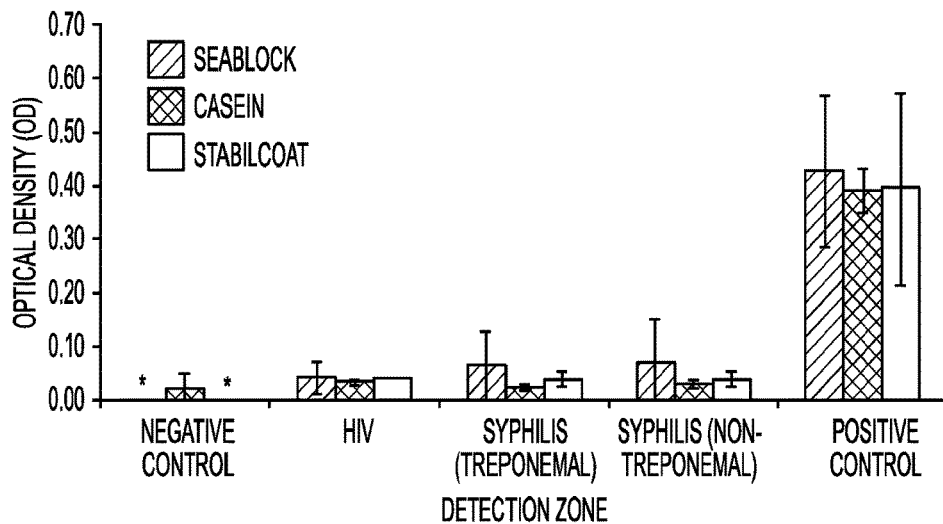
FIGS. 20A-20B are graphs of optical density (OD) measurements of microfluidic detections zones of a dongle device with various blocking agents for disease negative samples and HIV and syphilis disease positive samples, respectively, according to one or more embodiments of the disclosed subject matter.
Figure 20B:
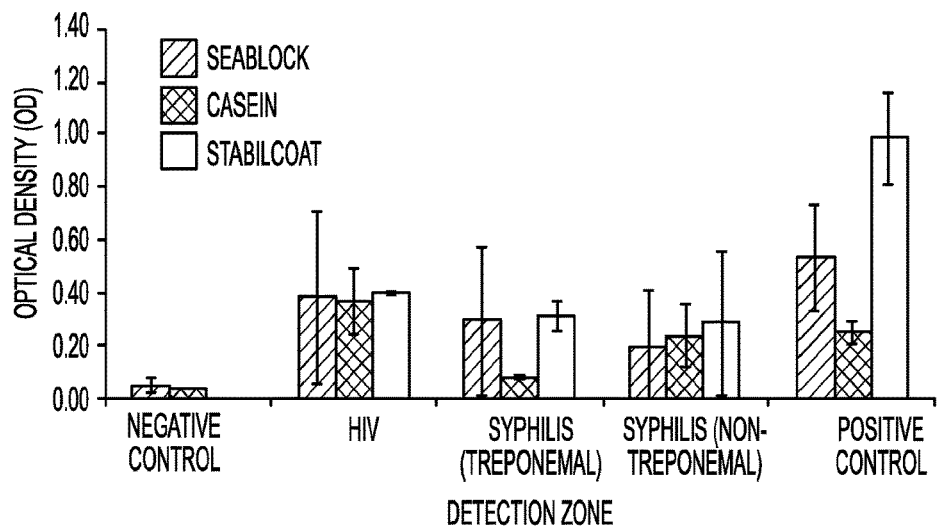

To mimic real testing conditions, cassettes were prepared ahead of time before transporting to the field. The disease-specific capture proteins were added tithe surface of the cassette by physisorption with a stabilizing agent (Stabil-Coat from Surmodics, blocking agent selection). FIGS. 20A-20B show a comparison of SeaBlock, casein and StabilCoat® as a blocking agent, using optical density measurements of microfluidic detection zones after testing. The results using disease negative sample are shown in FIG. 20A, while FIG. 20B shows the results using HIV and syphilis disease positive samples. Error bars indicate one standard deviation (n=2). Asterisks indicate an OD reading of zero.

For high-throughput manufacturing of chips, a robot-assisted manufacturing system 408 can be used for reproducible and high-throughput preparation of cassettes 406. An image of such a system is shown in FIGS. 19A-19B. Gold-labeled IgG and IgM antibodies were lyophilized inside plastic antibody holder 204. While in the field, each day prior to testing, two PBS-0.05% Tween-20 and four water washes as well as Silver reagent A and B were loaded to the reagent cassette manually by pipetting and sealed using an adhesive tape to mimic pre-packaged reagents.

As noted above, to perform the test, a user (e.g., HCW) collected fingerprick whole blood using conventional methods. Then, 1 µL of the whole blood was mixed with 9 µL of 1% BSA −0.05% Tween-20 in PBS. 2 µL of the mixed sample was pipetted onto the disposable cartridge to be run by the dongle. However, this dilution step may be eliminated as the cassette can use neat whole blood, as described above with respect to FIGS. 15A-15B. For example, chips prepared with a higher concentration of surface antigen may work well with undiluted whole blood samples. The user inserts the antibody holder 204 (pre-filled with 9 µL of 3% BSA −0.05% Tween in PBS) into a microfluidic cassette 206, inserts the cassette 206 into the dongle 202, and presses the bulb 220 fully to initiate vacuum. After 5 minutes, the user is prompted to move a toggle 250 to close a venting port and initiate silver development for the next 9 minutes. The whole test takes 15 minutes, after which results for all markers are available and clearly displayed on the screen.

Figures 4A, 4B:
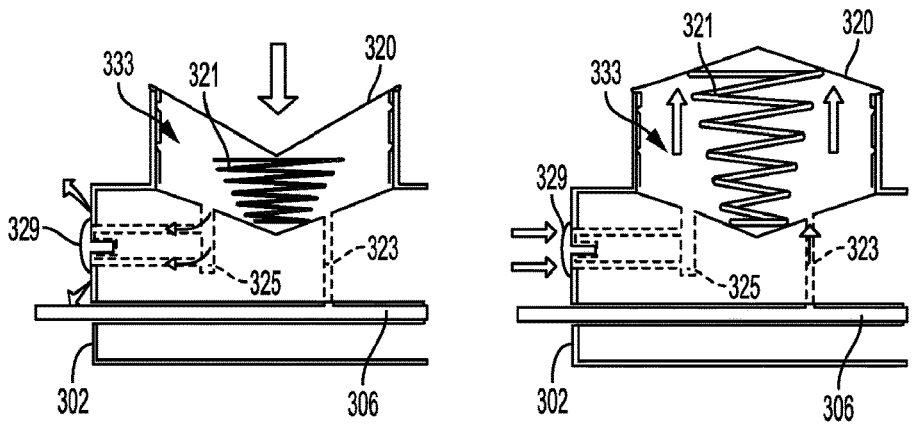
FIGS. 4A-4B illustrate actuation of a bulb of the diagnostic device to generate a negative pressure, according to one or more embodiments of the disclosed subject matter.

Embodiments of the disclosed dongle device and system include an electrical-power-free mechanically-activated vacuum source. For example, a reliable, repeatable vacuum can be generated at the time of the assay, while keeping the consumables simple to manufacture. Each test can include a) microfluidic cassette 206 with reagent holder on top and b) antibody holder 204 containing lyophilized gold and optionally a sample collector portion. Once the antibody holder 204 is attached, the microfluidic cassette 206 can be connected to the dongle 202. When the microfluidic chip 206 is fully inserted into the dongle 202, the microfluidic outlet can connect with the vacuum chamber. The user can initiate flow by pressing the bulb 220, which movement evacuates air from the vacuum chamber via the one-way valve. As the bulb re-expands, negative pressure can be generated in the vacuum chamber to enable flow of fluid, as illustrated in FIGS. 4A-4B. After sample and washes pass through (e.g., ~6 min), the user can be prompted to slide the toggle 250 to seal the venting port. The user can be prompted to re-initiate the vacuum by pressing the bulb, which can initiate movement and mixing of the two silver reagents and flow over the testing zones.

In the dongle device, each testing zone 312 can be sandwiched between an LED 322 and a photodiode 310 with a signal amplifying circuit. The light intensity can be measured before ($I_0$) and after ($I$) silver development, and absorbance value (optical density, or OD) can be calculated by:

$$OD = -\log\left(\frac{I}{I_0}\right)$$

The amount of analytes captured determines the amount of silver development, which in turn correlates with the absorbance value.

Recombinant multi-epitope chimeric antigens (gp41, gp36, and O-IDR) can be selected for an HIV 1/2 (Biolink International) marker, a 17-kDa recombinant outer membrane protein TpN17 (Lee Labs) for a treponemal syphilis marker, and synthetic cardiolipin prepared from plant source provided by CDC for a non-treponemal syphilis marker. An antibody against cardiolipin is used as a non-treponemal marker for syphilis. Cardiolipin, a lipoidal material, is released as a result of damage to the host cells because of the active infection and also from the cell surface of Treponemapallidum itself. It indicates active infection as well as a reinfection and is helpful in tracking the effectiveness of treatment, especially if patients are allergic to penicillin and must take other treatment instead. An anti-goat IgG antibody, binds to gold-labeled goat anti-human antibody (Life Technologies), was selected as an internal positive control. For an internal negative control (provide background signal), surface was not functionalized with any protein but treated with blocking agent, as illustrated schematically in FIG. 11.

Direct physisorption of antigens onto the plastic microfluidic cassettes can be used. For example, 2 µg/mL of HIV chimeric antigens, 15 µg/mL of TpN17, and 10 µg/mL of anti-goat IgG Ab in bicarbonate buffer solution were spotted on the detection zones using a robotic arm as an automated fluid dispenser. Different surface chemistries were used for cardiolipin functionalization on plastic surface. Cardiolipin was covalently attached to the plastic surface using EDC-Sulfo-NHS reaction, which activates the carboxylate groups on cardiolipin for binding with amine-groups on poly-L-lysine coated plastic. Other attachment techniques are also possible according to one or more contemplated embodiments.

To preserve the conformation and reactivity of the adsorbed antigens, the performance of three blocking/stabilizing agents were tested: casein (Thermo Scientific), Sea Block (Thermo Scientific) and StabilCoat Immunoassay Stabilizer® (Surmodics, Inc.). Cassettes were functionalized with the various protein markers as described above. For this experiment, fluid was dispensed by manual pipetting onto cassette surfaces. The blocking agent was then spotted on each detection zone and incubated for 1 hour at room temperature in a humid chamber. After incubation, the blocking agent solution was aspirated and plastic cassettes were placed in a vacuum desiccator for 20-30 minutes. The vacuum sealed chamber containing the microfluidic cassettes was then placed in a 30° C. oven for 4-6 hours of secondary drying. Cassettes were sealed with clear adhesive tape and stored at 4° C. until use. An HIV/Syphilis co-infected sera sample as well as a disease negative sera sample was tested on cassettes prepared with each blocking agent. Resulting OD signals for each detection zone were plotted, with error bars indicating one standard deviation (n=2, total 6 runs/sample) as shown in FIGS. 20A-20B.

In evaluating the blocking agents, the optimization goals for each detection zone were as follows: (1) minimize noise on the negative control zone; (2) minimize non-specific binding on target zones for tests with disease-negative samples; (3) maintain optimal conditions for antibody binding on target zones for tests with disease positive samples, and (4) maintain high positive control signals for all tests. Casein was observed to form particulates within the channels of the cassette detection zones after incubation and thus frequently inhibited flow even after secondary drying steps. While data was gathered for casein treated cassettes, there was a much higher rate of cassette failure due to flow issues and casein was not considered a viable blocking agent candidate for this platform. After running the disease-negative sample, StabilCoat® and Sea Block both had undetectable noise levels on the negative control zones, and all three agents resulted in the desired low target zone signals for HIV and Syphilis. After running the HIV/Syphilis co-infected sample, StabilCoat® treated cassettes had the strongest signals on target zones and positive control, the lowest noise level on the negative control and lower variance between runs. The larger deviations observed on the non-treponemal syphilis detection zone, was evident for all the cassettes, suggesting inhomogeneous cardiolipin attachment, perhaps due to the manual pipetting of fluids during cassette functionalization steps. StabilCoat® was selected as a viable blocking agent and used for ongoing experiments testing cassette stability.

The reagent cassette can include, for example, two PBS-Tween and four water washes as well as Silver reagent A and B. For example, the reagent cassette (see FIGS. 2B-2C) can be loaded by manually pipetting and sealing using an adhesive tape. Alternatively or additionally, industrial robotic techniques for loading reagents and apply adhesives can be employed for a high-throughput manufacturing.

Gold-labeled IgG/IgM antibodies can be employed in the dongle device. Anti-cardiolipin antibodies are commonly found IgM antibodies, and therefore, the addition of gold-labeled IgM offers enhanced sensitivity. Additional gold-labeled anti-hIgM does not provide a significant change in HIV signal, as most antibodies HIV IgG antibodies. Optionally, the gold-labeled antibodies as well as an anti-coagulant can be lyophilized onto the antibody holder for long term storage and ease of use for end-user. FIG. 13 shows no difference in signal from 5-month stored lyophilized gold-labeled antibodies and freshly prepared gold-labeled antibodies in buffer.

Figure 21:
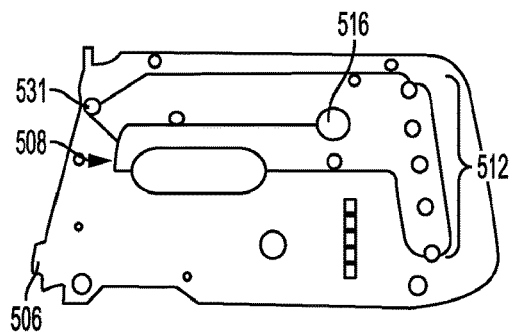
FIG. 21 is an image of another reagent cassette for combined HIV and anemia testing, according to one or more embodiments of the disclosed subject matter.

In one or more embodiments of the disclosed subject matter, the diagnostic device can be configured to perform a colorimetric assay to determine hemoglobin concentration (i.e., to test for anemia) in addition to other immunoassays, such as determining the presence of HIV or syphilis. FIG. 21 shows an image of a cassette 506 for such combined testing, where the microfluidic network 508 contained thereon has an inlet 531, outlet 516, and multiple detection zones 512. Referring to FIG. 3A again, for example, optical detection zone 312a can measure hemoglobin concentration and can include a 530 nm LED 322a and a green-sensitive (e.g., 570 nm) photodiode 310a. Optical detection zones 312b-312e can measure optical density of immunoassay zones and can include a 636 nm LED 322b-322e and a red-sensitive photodiode 310b-310e. LED control and photodiode readings can be programmed into a microcontroller, and photodiode readings can be read out to a separate processing device, such as a smartphone or computer.

The following lysis agents were tested: 3-[(3-Cholamidopropyl)dimethylammonio]-1-propanesulfonate (CHAPS, Sigma), Triton X-100 (Sigma), and sodium deoxycholate (Sigma). Each lysis agent was dissolved in 1× phosphate buffered saline (PBS) or deionized water at a range of concentrations, 8 µL placed in a microcentrifuge tube, and solvent was removed using a centrifugal evaporator. To lyse blood, 8 µL of fresh whole blood (collected within the past 3 days) was gently mixed in the microcentrifuge tube with the lysis agent. The sample was drawn into the microfluidic cassette by negative-pressure driven flow (~0.33 atm). Each sample was observed in the microfluidic channels under 10× magnification on a bright-field microscope, and blood was considered completely lysed if there were no visible red blood cells (RBCs).

Fresh whole blood was obtained via venipuncture from healthy donors via an IRB approved protocol. To simulate a range of hemoglobin concentrations, supernatant plasma was removed to concentrate the collected sample to ~20 g/dL. Hemoglobin concentrations ranging from 0 to 21 g/dL were created by diluting the blood with autologous plasma. To measure the hemoglobin concentration of a sample, 2 µL of 0.05% (v/v) Tween-20 in PBS was drawn through the microfluidic channel, and an initial intensity reading is taken ($I_{0,530}$). Next, blood was lysed with CHAPS by pipette mixing, and drawn through the microfluidic channel and a second intensity reading is taken while blood was flowing through the channel ($I_{530}$). The average of two readings from a HemocueHb 201+ was used as the reference value.

Hemoglobin concentration can be measured at the same time as HIV antibodies using lysed whole blood. Microfluidic cassettes can be prepared using disease-specific antigens functionalized on the plastic surface of microfluidic zones via direct adsorption: no antigen for negative control zone, 10 µg/mL of HIV 1/2 chimeric antigens (gp 41, gp 36, and O-IDR, Biolink International) for the HIV zone, and 25 µg/mL of rabbit anti-goat IgG antibody (Life Technologies) for the positive control zone. All zones can be treated for 1 hour with StabilCoat Immunoassay Stabilizer (Surmodics, Inc.) for stability and blocking. Whole blood samples were obtained from Columbia University Medical Center (CUMC) through an IRB approved protocol.

To run the assay, an initial wash of 2 µL of 0.05% Tween-20 in PBS can be drawn through the cassette. The blood sample can be gently mixed with dried lysis agent (e.g., on chip in the antibody holder, in the inlet of the cassette, or elsewhere, such as in a microcentrifuge tube). Then, 2 µL of lysed blood sample can be drawn through the microfluidic cassette. For hemoglobin measurement, an initial intensity reading ($I_{0,530}$) is taken during the Tween-20 wash, and another intensity reading ($I_{530}$) while the blood flowed through the cassette. Once the whole blood sample has flowed through, the remainder of the reagents can be delivered: 14.5 µL gold-labeled anti-IgM (0.27 µg/mL) and anti-IgG (0.53 µg/mL) antibodies (OPKO Diagnostics) in 3%-BSA-0.2% Tween-20 in PBS, two 2 µL 0.05% Tween-PBS washes, four 2 µL water washes, each separated by air spaces.

In the presence of disease-specific antibodies, gold-labeled secondary antibodies will bind to the zone surface. Subsequently, silver nitrate and reducing agents (OPKO Diagnostics) are drawn through the cassette, and silver ions will reduce on gold nanoparticles attached to the surface. An initial intensity reading ($I_{0,636}$) is taken immediately after silver has entered the channel, and another intensity reading ($I_{636}$) after 6 minutes of silver development. Lysis buffer optimization experiments were read on a bench-top analyzer (OPKO Diagnostics); the dual hemoglobin measurement and HIV immunoassay were performed on the dongle.

As noted above, the first optical zone can be dedicated to hemoglobin measurement: a green LED 322a (530 nm) is aligned directly atop the test zone 312a, with a 1 mm pinhole 380 and green-sensitive photodiode 310a (570 nm) aligned directly below the test zone 312a (FIG. 3A). When whole blood filled the test zone, hemoglobin absorbed the 530 nm light, proportionally reducing the light sensed by the photodiode. Samples with higher hemoglobin concentration showed higher absorbance, while samples with lower hemoglobin concentration showed correspondingly lower absorbance.

Lysis of RBC can enhance the reproducibility of measurements of hemoglobin concentrations by creating a homogenous hemoglobin solution for accurate correlation with absorbance readings. The lysis conditions to completely lyse red blood cells were: sodium deoxycholate (5% w/v, in PBS), CHAPS (48 mM, in PBS), Triton X-100 (10 mM, in PBS), and Triton X-100 (10 mM, in water). Sodium deoxycholate in water and CHAPS in water did not fully lyse blood. Blood mixed with dried PBS alone, or mixing alone also did not cause lysis.

Figure 22:
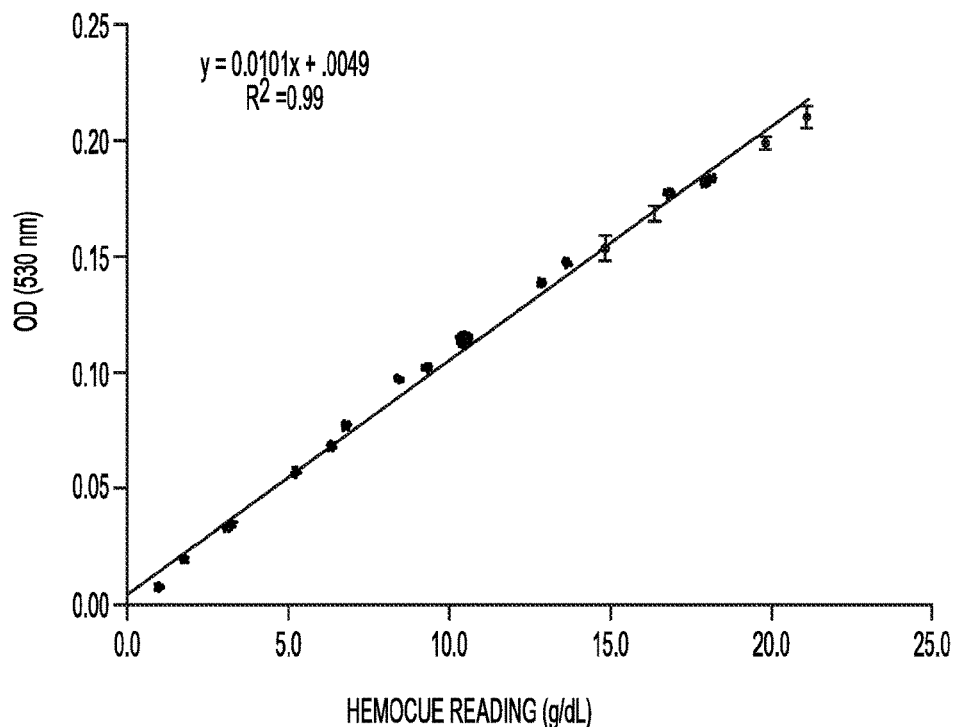
FIG. 22 is a graph of a calibration curve showing correlation between optical density measurements with standard Hemocue readings.

To generate a correlation between optical density and hemoglobin concentration, a range of simulated whole blood hemoglobin concentrations were tested (0-21.1 g/dL). Photodiode intensity readings were taken while channels were filled with a 0.05% Tween-20 PBS wash ($I_{0,530}$) and while channels were filled with lysed blood ($I_{530}$). Reagents flowed through channels with generated negative pressure, and readings were taken under constant flow. Optical densities obtained with the disclosed device showed a strong linear correlation ($R^2=0.99$) when compared to Hemocue readings, as shown in FIG. 22. The precise alignment of optics with repeatable microfluidic zones gave an average coefficient of variance of 1% between technical replicates.

Figure 23:
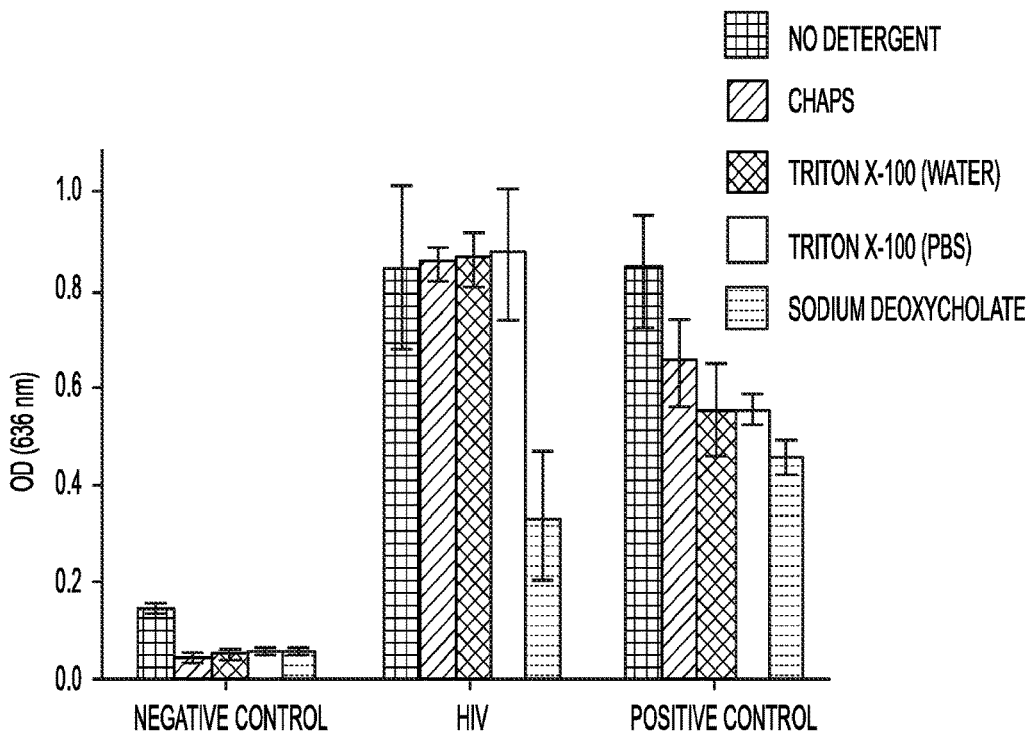
FIG. 23 is a graph comparing immunoassay signal (measured in optical density) of an HIV positive sample in the presence of five different lysis conditions: no lysis, 48 mM CHAPS in PBS, 10 mM Triton X-100 in H2O, 10 mM Triton X-100 in PBS, and 5% w/v sodium deoxycholate in PBS.

Since the immunoassay utilizes gold-labeled secondary antibodies with silver amplification, the presence of disease specific antibodies can be detected with simple optics. To assess the effect of lysis agents on the immunoassay, whole blood was mixed with sodium deoxycholate (5% w/v, in PBS), CHAPS (48 mM, in PBS), Triton X-100 (10 mM, in PBS), and Triton X-100 (10 mM, in water). In an initial screening of the four lysis conditions with an HIV positive sample, sodium deoxycholate significantly decreased the immunoassay signal, while CHAPS and Triton X-100 showed no significant difference, as illustrated in FIG. 23. Further, sodium deoxycholate increased the time to flow the blood sample through the channel by several fold, which would increase the assay time or even lead to clogging of the channels. On the other hand, CHAPS and Triton X-100 mixed with whole blood had approximately the same flow time as blood without lysis agent.

Figure 25:
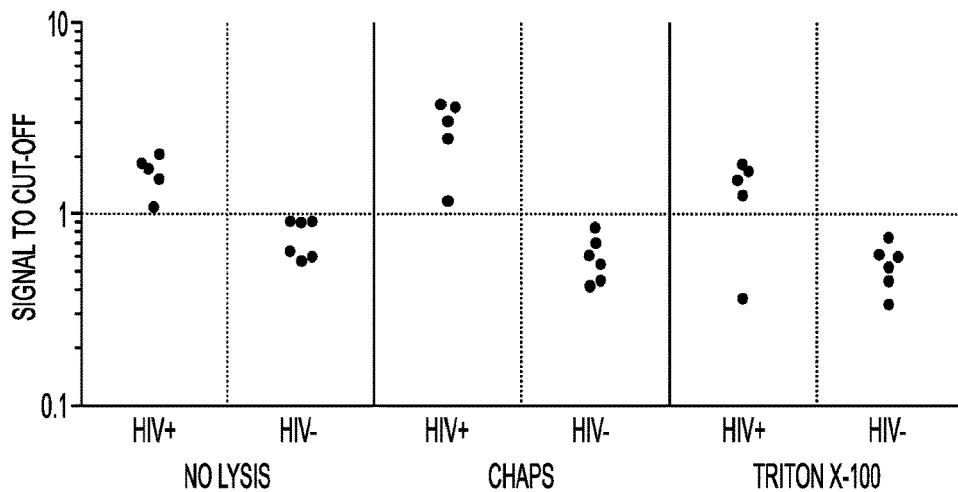
FIG. 25 is a graph comparing diagnostic accuracy using 11 whole blood samples (5 HIV positive, 6 HIV negative) under three lysis conditions: no lysis buffer, 48 mM CHAPS in PBS, and 10 mM Triton X-100 in water.

Eleven samples with no lysis buffer, CHAPS, and Triton X-100, were tested to see if clear separation between optical density of HIV positive and negative samples was preserved amongst a larger sample of patients. With both lysis buffers, some positive samples had decreased OD; however, the negative samples also had a much lower OD, preserving the separation. A cut-off point was selected for each data set that provided the best sensitivity and specificity. Without lysis buffer, the immunoassay showed 100% (95% CI: 48-100%) sensitivity and 100% (95% CI: 54-100%) specificity. Blood lysed with CHAPS (40 mM, PBS) showed 100% (95% CI: 48-100%) sensitivity and 100% (95% CI: 54-100%) specificity, and blood lysed with Triton X-100 (10 mM, water) showed 80% (95% CI: 28-99%) sensitivity and 100% (95% CI: 54-100%) specificity, as shown in FIG. 25.

In one or more embodiments, CHAPS (48 mM, in PBS) can thus be selected as the lysis buffer since it preserves diagnostic accuracy, even increasing the signal-to-cut off ratio in several positive samples. The positive control signal was decreased with CHAPS, however, it still provided a strong enough signal to indicate that the immunoassay had been executed properly. To enhance ease of use for the end user, CHAPS or other lysis agent can be lyophilized within the sample collection system, similar to other reagents/antibodies used within the system, thereby allowing for hemoglobin measurement without any additional steps to the user.

Figure 24A:
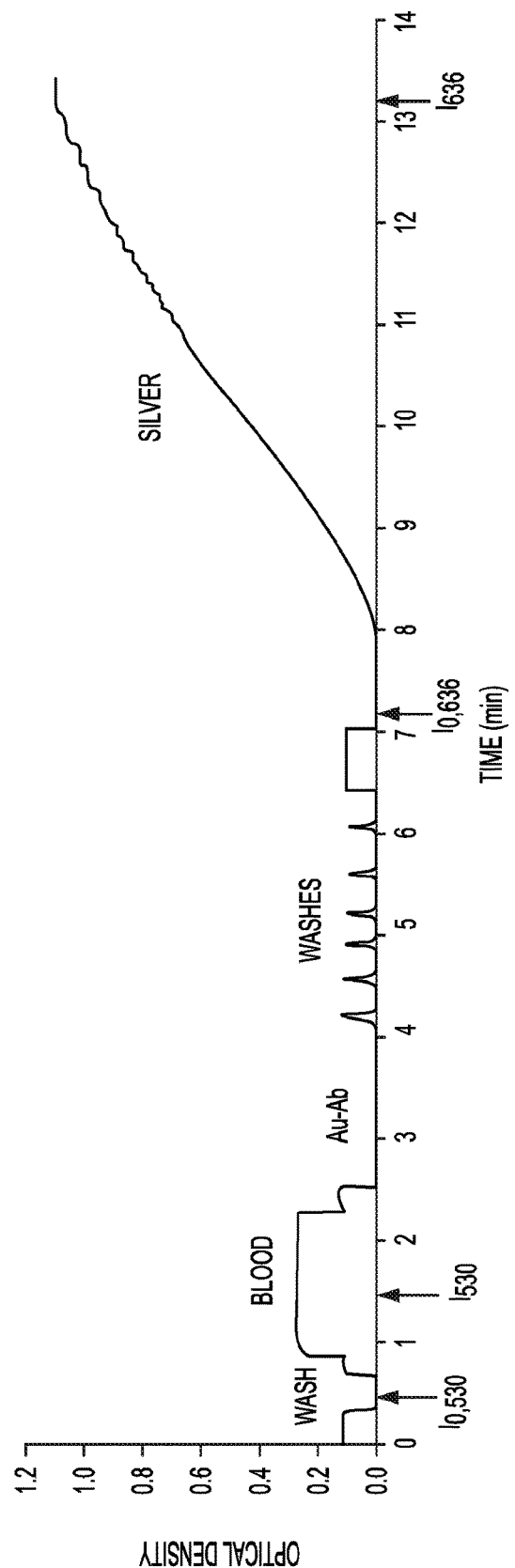
FIG. 24A is a graph of photodiode readings in a combined HIV/anemia diagnostic device, according to one or more embodiments of the disclosed subject matter.
Figure 26:
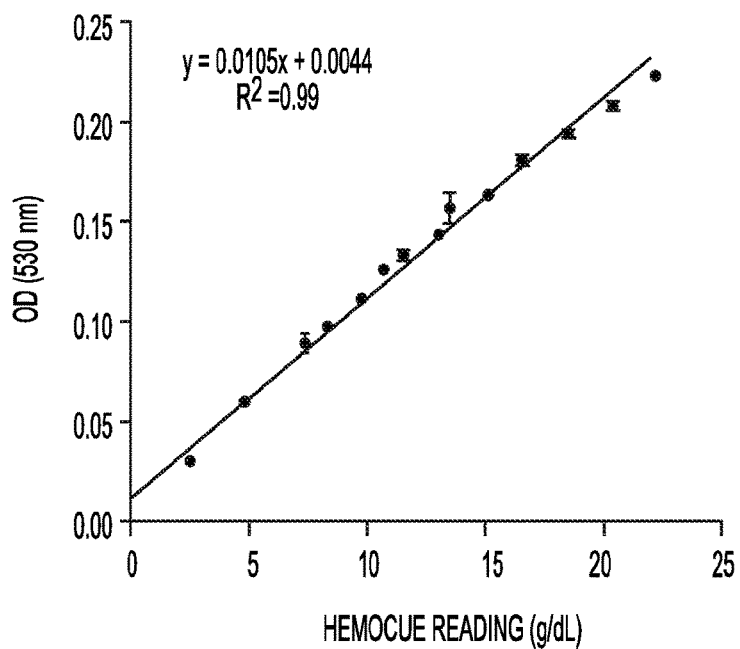
FIG. 26 is a graph showing a calibration curve for another diagnostic device showing correlation between optical density measurements and standard Hemocue readings.

The hemoglobin measurement and HIV dual-assay was then validated on 38 clinical samples. For hemoglobin measurements, the dongle took photodiode readings, while 0.05% Tween-20 PBS filled the channel ($I_{0,530}$) and while the whole blood sample filled the channel ($I_{530}$). Next, gold-labeled secondary antibodies, washes, and silver amplification reagents flowed through the channel. The dongle took photodiode readings as soon as silver reagents filled the channel ($I_{0,636}$) and 6 minutes after ($I_{636}$), as illustrated in FIG. 24A. Reagents flowed through the channel with generated negative pressure, and all readings were again taken under constant flow. Estimated hemoglobin measurements were calculated based on the line of best fit from the calibration curve, as shown in FIG. 22. Samples 14-38 were performed on a different device, and estimated hemoglobin was calculated with a device specific calibration curve, as shown in FIG. 26.

Figure 24B:
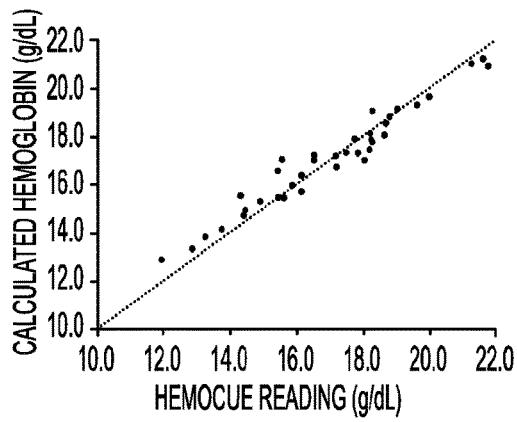
FIG. 24B is a graph comparing Hemocue readings with hemoglobin calculated based on optical density readings in a combined HIV/anemia diagnostic device, according to one or more embodiments of the disclosed subject matter.
Figure 24C:
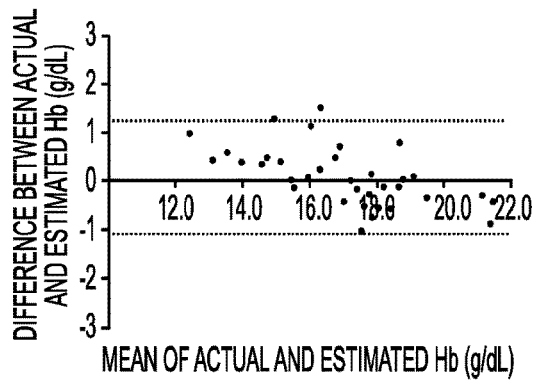
FIG. 24C is a Bland-Altman plot comparing mean of actual and estimated hemoglobin with difference between actual and estimated hemoglobin concentration measured using the combined HIV/anemia diagnostic device, according to one or more embodiments of the disclosed subject matter.
Figure 24D:
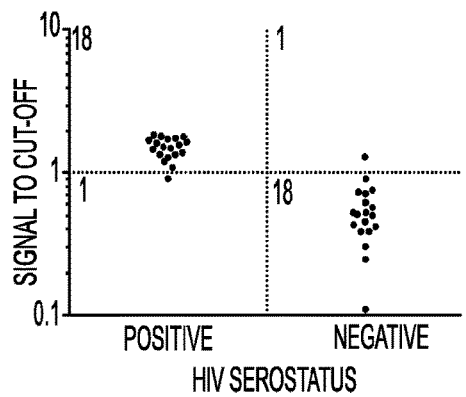
FIG. 24D is a dot plot showing signal-to-cutoff ratios for 19 HIV positive and 19 HIV negative samples in a combined HIV/anemia diagnostic device, according to one or more embodiments of the disclosed subject matter.
Figure 24E:
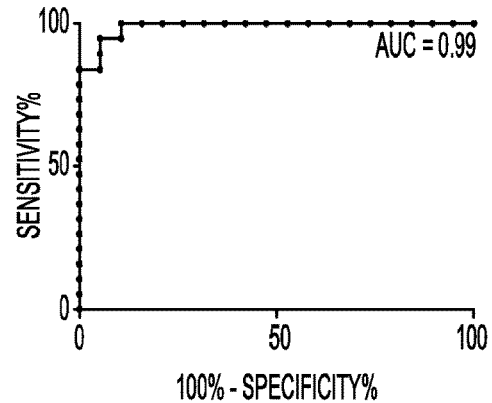
FIG. 24E is a receiver operating characteristic curve (ROC curve) of results shown in FIG. 24D.

Estimated hemoglobin concentration showed strong agreement when compared with Hemocue readings, as shown in FIG. 24B. Estimated hemoglobin showed a bias of 0.07 g/dL and 95% limits of agreement between −1.08 to 1.22 g/dL, as shown in FIG. 24C. Only 34 of 38 samples were within 7% of the target. The average difference from target was 2.8±2.4% of target concentration. While complete blood count (CBC) results were available for most samples, the reported hemoglobin value on CBC was often several g/dL lower than the result given by Hemocue, likely because plasma had been taken from the sample for other testing. The average of two readings from a HemocueHb 201+ was used as the reference hemoglobin concentration. Reference results for HIV status were determined on Abbott ARCHITECT. The HIV immunoassay showed sensitivity of 95% (95% CI: 74-100%) and specificity of 95% (95% CI: 74-100) and area under curve (AUC) of 0.99, as shown in FIGS. 24D-24E. The full table of results is provided in Table 1 below.

TABLE 1

HIV immunoassay and HIV concentration results obtained from the dongle for 38 clinical samples.

| | Dongle Results | | Reference | |
| --- | --- | --- | --- | --- |
| | | Estimated | | |
| Sample # | HIV (signal to cutoff) | Hemoglobin (g/dL) | HIV Status | Hemoglobin (g/dL) |
| 1 | 0.90 | 21.2 | Pos | 21.7 |
| 2 | 1.20 | 20.9 | Pos | 21.8 |
| 3 | 1.46 | 18.1 | Pos | 18.7 |
| 4 | 1.61 | 18.1 | Pos | 18.3 |
| 5 | 1.47 | 19.1 | Pos | 18.3 |
| 6 | 1.65 | 21.0 | Pos | 21.3 |
| 7 | 1.33 | 18.8 | Pos | 18.8 |
| 8 | 1.78 | 16.4 | Pos | 16.2 |
| 9 | 1.81 | 17.9 | Pos | 17.8 |
| 10 | 1.33 | 17.3 | Pos | 16.6 |
| 11 | 1.09 | 19.7 | Pos | 20.0 |
| 12 | 1.69 | 19.1 | Pos | 19.1 |
| 13 | 1.39 | 19.3 | Pos | 19.7 |
| 14 | 0.61 | 12.9 | Neg | 12.0 |
| 15 | 0.73 | 16.0 | Neg | 15.9 |
| 16 | 0.52 | 14.9 | Neg | 14.5 |
| 17 | 0.30 | 14.2 | Neg | 13.8 |
| 18 | 0.38 | 17.3 | Neg | 17.5 |
| 19 | 1.77 | 17.5 | Pos | 18.2 |
| 20 | 1.75 | 15.3 | Pos | 14.9 |
| 21 | 1.29 | 17.8 | Pos | 18.3 |
| 22 | 1.56 | 17.2 | Pos | 17.2 |
| 23 | 1.47 | 16.8 | Pos | 17.2 |
| 24 | 1.67 | 13.3 | Pos | 12.9 |
| 25 | 0.71 | 15.6 | Neg | 14.3 |
| 26 | 0.74 | 16.6 | Neg | 15.5 |
| 27 | 0.91 | 18.6 | Neg | 18.7 |
| 28 | 0.52 | 15.5 | Neg | 15.6 |
| 29 | 0.39 | 17.0 | Neg | 16.6 |
| 30 | 0.51 | 17.3 | Neg | 17.9 |
| 31 | 0.45 | 16.0 | Neg | 16.0 |
| 32 | 0.11 | 14.7 | Neg | 14.4 |
| 33 | 0.43 | 13.8 | Neg | 13.3 |
| 34 | 0.50 | 17.0 | Neg | 18.1 |
| 35 | 0.42 | 17.9 | Neg | 18.3 |
| 36 | 0.25 | 15.7 | Neg | 16.2 |
| 37 | 0.57 | 15.5 | Neg | 15.5 |
| 38 | 1.28 | 17.1 | Neg | 15.6 |

To perform multiple types of tests in one platform, the chemistry of the different tests (including lysis, signal amplification, and washings) should be mutually compatible, and different concepts for signal readouts must be integrated within the same hardware instrumentation. In embodiments of the disclosed diagnostic device, photodiode readings for hemoglobin measurement can occur simultaneously with steps in the immunoassay, adding no additional time to the assay. Moreover, LED power and photodiode readings consumed only 8.5 mW over an additional 1.6 s, which is a negligible addition to the 0.22 mWh test. The hemoglobin test added no extra cost to the hardware and negligible added per-test cost for CHAPS, while replacing a diagnostic test that typically costs $1 per test run with an $800 reader.

Figures 27A, 27B:
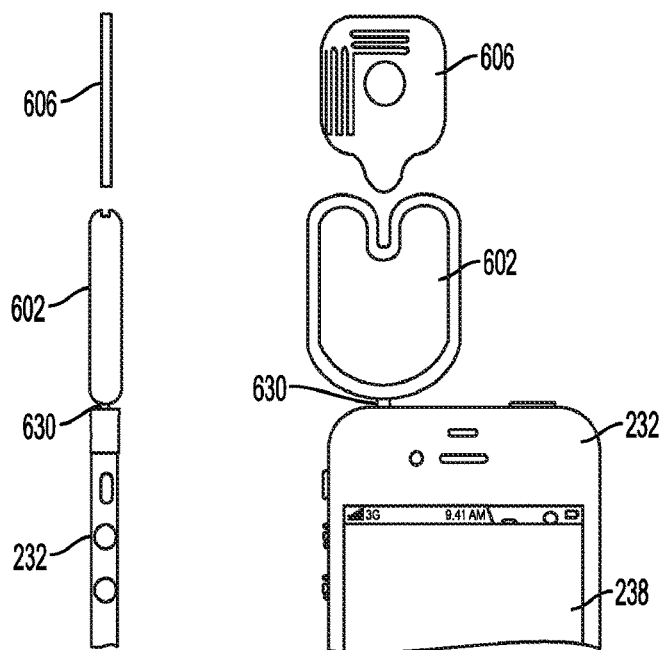
FIGS. 27A-27B are side and front views, respectively, of an alternative configuration for a smartphone dongle device and microfluidic cassette, according to one or more embodiments of the disclosed subject matter.

FIGS. 27A-27B illustrate a further embodiment of the disclosed dongle device 602 and that further miniaturizes the dongle 602 while maintaining high diagnostic performance. In particular, as with other embodiments, a cassette 606 including a microfluidic network can be inserted into the dongle device 602, which is coupled to a smartphone or PDA 232 via audio jack 630. FIG. 18A-18B shows the results of the miniaturized dongle in testing for HIV in whole blood. The vertical scatter plot of silver absorbance for positive and negative HIV specimens is shown in the top plot of FIG. 18A, and the receiver-operating characteristic (ROC) curve show 100% sensitivity and specificity is shown in FIG. 18B.

Although applications of the diagnostic device in detecting HIV and syphilis and measuring hemoglobin concentration have been explicitly discussed above, embodiments of the disclosed subject matter are not limited thereto. Rather, the disclosed device could potentially be expanded to any application with a colorimetric readout, including measurements of concentrations of glucose, total protein, and serum iron levels, according to one or more contemplated embodiments. When combined with an immunoassay, this disclosed diagnostic device can bring a broad range of diagnostic panels to the point of care.

The foregoing descriptions apply, in some cases, to examples generated in a laboratory, but these examples can be extended to production techniques. For example, where quantities and techniques apply to the laboratory examples, they should not be understood as limiting.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, diagnostic devices, methods and systems. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

It will be appreciated that the modules, processes, systems, and sections described above can be implemented in hardware, hardware programmed by software, software instruction stored on a non-transitory computer readable medium or a combination of the above. For example, a method for operating a diagnostic instrument can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of controls and instruments and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, diagnostic devices, methods, and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

In one or more first embodiments, a handheld diagnostic system includes a reagent cassette includes a microfluidic network having an inlet, an outlet, and a detection region, the detection region including a plurality of detection zones, an antibody holder having a plurality of labeled antibodies therein and an outlet configured to interface with the inlet of the reagent cassette to deliver the antibodies to the microfluidic network; and a diagnostic dongle includes a recess, a manually-actuated pressure system, an array of light sources, an array of photodetectors, a control module, and an input/output connector. The detection zones are aligned with a respective light source and photodetector pair of the arrays when the cassette is inserted into the recess of the diagnostic dongle. The manually-actuated pressure system applies a negative pressure to the microfluidic network via the outlet of the reagent cassette to move fluids therethrough. The reagent cassette includes reagents and a lysis agent for whole blood. The detection region includes at least a first detection zone as a hemoglobin testing zone with no antigens thereon, a second detection zone having an antigen specific for HIV thereon, and a third detection zone having an antigen specific for syphilis thereon. The light source and photodetector pair aligned with the first detection zone includes a green-light-emitting light source and a green-sensitive photodetector. Each of the light source and photodetector pairs aligned with the second and third detection zones includes a red-light-emitting light source and a red-sensitive photodetector. The control module controls the respective pairs of light sources and photodetectors to interrogate the first detection zone to perform a colorimetric assay and the second and third detection zones to perform an immunoassay. Electrical power for the diagnostic dongle is provided exclusively via the input/output connector. The control module is configured to convert data of results of the colorimetric assay and immunoassay by frequency-shift keying (FSK) and to transmit the FSK-converted data via the input/output connector. Other communication protocols are also possible. Also, the respective light sources and detectors that form pairs are not necessarily distinct for each detection zone.

The first embodiments or any other embodiment, may further include a smartphone or personal digital assistant (PDA) that couples to the input/output connector to provide the electrical power and/or transmit data.

The first embodiments or any other embodiments may include variants in which the input/output connector is configured to interface with an audio port or a USB port of the smartphone or PDA. The first embodiments or any other embodiments may include variants in which the input/output connector includes an audio jack. The first embodiments or any other embodiments may include variants in which the diagnostic device and the smartphone or PDA are constructed to be held and operated by a user at the same time using a single hand. The first embodiments or any other embodiments may include variants in which the diagnostic device and the smartphone or PDA are constructed to be held and operated by a user at the same time using one hand to operate the manually-actuated pressure system and another hand to operate the smartphone or PDA. The first embodiments or any other embodiments may include variants in which the antigens in the second and third detection zones comprise disease-specific capture proteins that have been adhered to channel walls of the microfluidic network via physisorption. The first embodiments or any other embodiments may include variants in which the detection region further includes fourth and fifth detection zones operating as negative and positive control zones, respectively. The first embodiments or any other embodiments may include variants in which the positive control zone has rabbit anti-goat IgG antibody thereon and the negative control zone is free of antibodies. The first embodiments or any other embodiments may include variants in which the manually-actuated pressure system includes a manually displaceable bulb covering a pressure chamber with a spring therein, wherein the negative pressure is generated by manually depressing the bulb. The first embodiments or any other embodiments may include variants in which the labeled antibodies are gold-labeled antibodies. The first embodiments or any other embodiments may include variants in which the labeled antibodies include IgM antibodies. The first embodiments or any other embodiments may include variants in which the reagents comprise a silver reagent. The first embodiments or any other embodiments may include variants in which the reagents comprise silver nitrate and/or reducing agents. The first embodiments or any other embodiments may include variants in which the reagents and/or the lysis agent in the reagent cassette have been lyophilized prior to use in the diagnostic system. The first embodiments or any other embodiments may include variants in which the reagent cassette further includes a buffer therein. The first embodiments or any other embodiments may include variants in which the buffer includes bovine serum albumin (BSA) and/or polyoxyethylene sorbitan monopalmitate (TWEEN) in a phosphate buffered saline (PBS). The first embodiments or any other embodiments may include variants in which the lysis agent includes at least one of 3-[(3-cholamidopropyl)dimethyammonio]-1-propanesulfonate (CHAPS), sodium deoxycholate, and polyethylene glycol p-(1,1,3,3-tetramethylbutyl)-phenyl ether (TRITION X-100) in at least one of water and phosphate buffered saline (PBS). The first embodiments or any other embodiments may include variants in which the lysis agent includes 3-[(3-cholamidopropyl)dimethyammonio]-1-propanesulfonate (CHAPS) in phosphate buffered saline (PBS). The first embodiments or any other embodiments may include variants in which the light source aligned with the first detection zone emits light having a wavelength of 530 nm. The first embodiments or any other embodiments may include variants in which the light sources aligned with the second and third detection zones each emit light having a wavelength of 636 nm. The first embodiments or any other embodiments may include variants in which each of the light sources is a light-emitting diode (LEDs) or laser diode. The first embodiments or any other embodiments may include variants in which each of the photodetectors is a photodiode. The first embodiments or any other embodiments may include variants in which a pinhole aperture is provided in the optical path between each of the detection zones and its corresponding photodetector.

In one or more second embodiments, a diagnostic method includes depositing a sample of whole blood from a patient at an inlet of a reagent cassette, the reagent cassette includes a microfluidic network having the inlet, an outlet, and a detection region, the detection region including a plurality of detection zones. The method further includes coupling an outlet of an antibody holder to the inlet of the reagent cassette and inserting the reagent cassette into a recess of a diagnostic dongle, the diagnostic dongle includes a manually-actuated pressure system, an array of light sources, an array of photodetectors, a control module, and an input/output connector, the inserting being such that the detection zones are aligned with a respective light source and photodetector pair of the arrays. The method further includes actuating the pressure system using a single hand to generate a negative pressure at the outlet of the microfluidic network. The method further includes using the negative pressure to flow the whole blood from the inlet to the detection zones, after the flowing of the whole blood, flowing a plurality of labeled antibodies from, the antibody holder to the detection zones, and after the flowing of the labeled antibodies, flowing reagents and/or reducing agents to the detection zones. The method further includes illuminating each detection zone with light from a light source and detecting light transmitted through each detection zone by a corresponding photodetector and generating colorimetric or immunoassay data corresponding to each detection zone responsively to the detected light by the corresponding photodetector.

The second embodiments or any other embodiments may include variants in which the detection region includes at least a first detection zone as a hemoglobin testing zone with no antigens thereon, a second detection zone having an antigen specific for HIV thereon, and a third detection zone having an antigen specific for syphilis thereon. The colorimetric data may be generated for the first detection zone and indicates amount of hemoglobin in the whole blood and the immunoassay data may be generated for the second and third detection zones and indicate the presence of HIV and syphilis, respectively, in the whole blood.

The second embodiments or any other embodiments may include variants in which the light source and photodetector pair aligned with the first detection zone includes a green-light-emitting light source and a green-sensitive photodetector, and each of the light source and photodetector pairs aligned with the second and third detection zones includes a red-light-emitting light source and a red-sensitive photodetector. The second embodiments or any other embodiments may include variants in which the illuminating and detecting for the colorimetric assay is performed prior to the illuminating and detecting for the immunoassay. The second embodiments or any other embodiments may include variants in which the illumination and detecting includes illuminating and detecting at a first time prior to flowing of the whole blood, illuminating and detecting at a second time after the first time and during the flowing of the whole blood, illuminating and detecting at a third time after the second time and before the flowing of the reagents, and illuminating and detecting at a fourth time after the third time and during the flowing of the reagents. The first and second times are used to generate the colorimetric data. Data of the third and fourth times are used to generate the immunoassay data.

The second embodiments or any other embodiments may include variants that include converting the colorimetric or immunoassay data by frequency-shift keying (FSK) and transmitting the FSK-converted data via an input/output connector of the diagnostic dongle. The second embodiments or any other embodiments may include variants that include lysing the whole blood before it reaches the detection zone. The second embodiments or any other embodiments may include variants in which the lysing is performed by a lysis agent within the microfluidic network. The second embodiments or any other embodiments may include variants in which the lysis agent includes at least one of 3-[(3-cholamidopropyl)dimethyammonio]-1-propanesulfonate (CHAPS), sodium deoxycholate, and polyethylene glycol p-(1,1,3,3-tetramethylbutyl)-phenyl ether (TRITION X-100) in at least one of water and phosphate buffered saline (PBS). The second embodiments or any other embodiments may include variants in which the lysis agent includes 3-[(3-cholamidopropyl)dimethyammonio]-1-propanesulfonate (CHAPS) in phosphate buffered saline (PBS). The second embodiments or any other embodiments may include variants that include coupling a smartphone or personal digital assistant (PDA) to an input/output connector to provide electrical power to the diagnostic dongle and/or transmit data from the diagnostic dongle. The second embodiments or any other embodiments may include variants in which the input/output connector is configured to interface with an audio port or a USB port of the smartphone or PDA. The second embodiments or any other embodiments may include variants in which the input/output connector includes an audio jack. The second embodiments or any other embodiments may include variants in which the actuating the pressure system is performed using a single hand while using the same hand to hold the diagnostic device and the smartphone or PDA. The second embodiments or any other embodiments may include variants in which the actuating the pressure system is performed using one hand while using another hand to hold the diagnostic device and the smartphone or PDA. The second embodiments or any other embodiments may include variants in which antigens in the detection region comprise disease-specific capture proteins that have been adhered to channel walls of the microfluidic network via physisorption. The second embodiments or any other embodiments may include variants in which the actuating the pressure system includes manually depressing a bulb covering a pressure chamber with a spring therein to generate the negative pressure. The second embodiments or any other embodiments may include variants in which the labeled antibodies are gold-labeled antibodies. The second embodiments or any other embodiments may include variants in which the labeled antibodies include IgM antibodies. The second embodiments or any other embodiments may include variants in which the reagents comprise a silver reagent. The second embodiments or any other embodiments may include variants in which the reagents comprise silver nitrate and/or reducing agents. The second embodiments or any other embodiments may include variants in which between the flowing the plurality of labeled antibodies and the flowing reagents and/or reducing agents, the negative pressure is used to flow one or more washes. The second embodiments or any other embodiments may include variants in which each wash is separated by an air space. The second embodiments or any other embodiments may include variants in which the one or more washes includes at least one wash of bovine serum albumin (BSA) and/or polyoxyethylene sorbitan monopalmitate (TWEEN) in a phosphate buffered saline (PBS) followed by at least one wash of water. The second embodiments or any other embodiments may include variants in which the reagents and/or the lysis agent in the reagent cassette have been lyophilized prior to use, the method further includes hydrating the reagent cassette prior to the depositing the sample. The second embodiments or any other embodiments may include variants in which the light source and photodetector pair aligned with the first detection zone includes an LED emitting light having a wavelength of 530 nm and a green-sensitive photodetector, and each of the light source and photodetector pairs aligned with the second and third detection zones includes an LED emitting light having a wavelength of 636 nm and a red-sensitive photodetector.

In one or more third embodiments, a handheld diagnostic system includes a reagent cassette includes a microfluidic network having an inlet, an outlet, and a detection region, the detection region including at least one detection zone. A diagnostic dongle has a recess, a manually-actuated pressure system, at least one light source, at least one photodetector, a control module, and an input/output connector. The at least one detection zone is aligned with a respective photodetector when the cassette is inserted into the recess of the diagnostic dongle. The manually-actuated pressure system applies a pressure to the microfluidic network of the reagent cassette to move fluids therethrough. The reagent cassette includes reagents and/or a lysis agent for whole blood. The control module controls the at least one light source and the at least one photodetector to interrogate the respective detection zone to perform at least one of a colorimetric assay, an immunoassay, an electrochemical assay, and absorbance detection.

The third embodiments or any other embodiments may include variants that include a smartphone or personal digital assistant (PDA) that couples to the input/output connector to provide electrical power to the diagnostic dongle and/or transmit data from the diagnostic dongle. The third embodiments or any other embodiments may include variants in which the input/output connector is configured to interface with an audio port or a USB port of the smartphone or PDA. The third embodiments or any other embodiments may include variants in which the input/output connector includes an audio jack. The third embodiments or any other embodiments may include variants in which the diagnostic device and the smartphone or PDA are constructed to be held and operated by a user at the same time using a single hand. The third embodiments or any other embodiments may include variants in which the diagnostic device and the smartphone or PDA are constructed to be held and operated by a user at the same time using one hand to operate the manually-actuated pressure system and another hand to operate the smartphone or PDA. The third embodiments or any other embodiments may include variants in which electrical power for the diagnostic dongle is provided exclusively via the input/output connector The third embodiments or any other embodiments may include variants in which the control module is configured to convert data of results of the colorimetric assay and immunoassay by frequency-shift keying (FSK) and to transmit the FSK-converted data via the input/output connector. The third embodiments or any other embodiments may include variants that include an antibody holder having a plurality of labeled antibodies therein and an outlet configured to interface with the inlet of the reagent cassette to deliver the antibodies to the microfluidic network. The third embodiments or any other embodiments may include variants in which antigens in the at least one detection zone comprise disease-specific capture proteins that have been adhered to channel walls of the microfluidic network via physisorption. The third embodiments or any other embodiments may include variants in which the detection region further includes detection zones operating as negative and positive control zones. The third embodiments or any other embodiments may include variants in which the manually-actuated pressure system includes a manually displaceable bulb covering a pressure chamber with a spring therein, wherein the pressure is generated by manually depressing the bulb. The third embodiments or any other embodiments may include variants in which a pinhole aperture is provided in the optical path between each of the detection zones and its corresponding photodetector. The third embodiments or any other embodiments may include variants in which the manually-actuated pressure system applies a negative pressure to the microfluidic network.

In one or more fourth embodiments, a diagnostic method includes depositing a sample of whole blood from a patient at an inlet of a reagent cassette, the reagent cassette includes a microfluidic network having the inlet, an outlet, and a detection region, the detection region including at least one detection zone. The method further includes inserting the reagent cassette into a recess of a diagnostic dongle, the diagnostic dongle includes a manually-actuated pressure system, at least one light source, at least one photodetector, a control module, and an input/output connector, the inserting being such that each detection zone is aligned with a respective photodetector. The method further includes manually actuating the pressure system to generate a pressure in the microfluidic network. The method further includes using the generated pressure to flow the whole blood from the inlet to the detection zones and after the flowing of the whole blood, flowing reagents and/or reducing agents to the detection zones. The method further includes illuminating each detection zone with light from at least one light source and detecting light transmitted through each detection zone by a respective photodetector. The method further includes using the illuminating and detecting to perform at least one of colorimetric assay, an immunoassay, an electrochemical assay, and absorbance detection for each detection zone, and generating data responsively to the detected light by the respective photodetector.

The fourth embodiments or any other embodiments may include variants that include coupling an outlet of an antibody holder to the inlet of the reagent cassette, and using the generated pressure to flow a plurality of labeled antibodies from the antibody holder to the detection zones after the flowing of the whole blood. The fourth embodiments or any other embodiments may include variants in which the manually actuating generates a negative pressure at the outlet of the microfluidic network. The fourth embodiments or any other embodiments may include variants that include coupling a smartphone or personal digital assistant (PDA) to the input/output connector to provide electrical power to the diagnostic dongle and/or transmit data from the diagnostic dongle. The fourth embodiments or any other embodiments may include variants in which the illuminating and detecting for the colorimetric assay is performed prior to the illuminating and detecting for the immunoassay. The fourth embodiments or any other embodiments may include variants in which the illumination and detecting includes illuminating and detecting at a first time prior to flowing of the whole blood, illuminating and detecting at a second time after the first time and during the flowing of the whole blood, illuminating and detecting at a third time after the second time and before the flowing of the reagents, and illuminating and detecting at a fourth time after the third time and during the flowing of the reagents. Data of the first and second times is used to generate colorimetric data. Data of the third and fourth times is used to generate immunoassay data.

The fourth embodiments or any other embodiments may include variants that include converting the generated data by frequency-shift keying (FSK) and transmitting the FSK-converted data via the input/output connector of the diagnostic dongle. The fourth embodiments or any other embodiments may include variants that include lysing the whole blood before it reaches the detection zone. The fourth embodiments or any other embodiments may include variants in which the lysing is performed by a lysis agent within the microfluidic network. The fourth embodiments or any other embodiments may include variants in which the lysis agent includes at least one of 3-[(3-cholamidopropyl)dimethyammonio]-1-propanesulfonate (CHAPS), sodium deoxycholate, and polyethylene glycol p-(1,1,3,3-tetramethylbutyl)-phenyl ether (TRITION X-100) in at least one of water and phosphate buffered saline (PBS). The fourth embodiments or any other embodiments may include variants in which the lysis agent includes 3-[(3-cholamidopropyl)dimethyammonio]-1-propanesulfonate (CHAPS) in phosphate buffered saline (PBS). The fourth embodiments or any other embodiments may include variants in which the manually actuating the pressure system is performed using a single hand while using the same hand to hold the diagnostic device. The fourth embodiments or any other embodiments may include variants in which the manually actuating the pressure system is performed using one hand while using another hand to hold the diagnostic device. The fourth embodiments or any other embodiments may include variants in which antigens in the detection region comprise disease-specific capture proteins that have been adhered to channel walls of the microfluidic network via physisorption. The fourth embodiments or any other embodiments may include variants in which the manually actuating the pressure system includes manually depressing a bulb covering a pressure chamber with a spring therein to generate the negative pressure. The fourth embodiments or any other embodiments may include variants in which before the flowing reagents and/or reducing agents, the pressure is used to flow one or more washes. The fourth embodiments or any other embodiments may include variants in which each wash is separated by an air space. The fourth embodiments or any other embodiments may include variants in which the one or more washes includes at least one wash of bovine serum albumin (BSA) and/or polyoxyethylene sorbitan monopalmitate (TWEEN) in a phosphate buffered saline (PBS) followed by at least one wash of water.

In one or more fifth embodiments, a diagnosis method includes using one hand to hold and manually actuate a mechanism of a diagnostic device to generate a negative pressure that pulls a sample into a detection zone and performing an assay on the sample in the detection zone to generate data. The method further includes transmitting the data from the diagnostic device to a smart-enabled device via connection between the diagnostic device and the smart-enabled device while also receiving power for the diagnostic device via the connection.

The fifth embodiments or any other embodiments may include variants in which the mechanism to generate a negative pressure includes a bulb covering a pressure chamber with a spring therein, wherein the negative pressure is generated by depressing the bulb. The fifth embodiments or any other embodiments may include variants in which the connection between the diagnostic device and the smart-enabled device includes an audio jack. The fifth embodiments or any other embodiments may include variants in which the transmitting the data includes converting the data via frequency-shift keying for transmission via the connection. The fifth embodiments or any other embodiments may include variants in which the assay includes at least one of absorbance measurements, immunoassay, colorimetry, and electrochemical detection. The fifth embodiments or any other embodiments may include variants in which the assay includes a diagnostic test for at least one of human immunodeficiency virus (HIV), syphilis, anemia, glucose, total protein, and serum iron. The fifth embodiments or any other embodiments may include variants in which the diagnostic device obtains all of its electrical power requirements via the received power. The fifth embodiments or any other embodiments may include variants in which at least three assays for detecting different diseases are simultaneously performed on the sample. The fifth embodiments or any other embodiments may include variants in which the assay uses gold-labeled IgM antibodies. The fifth embodiments or any other embodiments may include variants that includes, prior to the performing an assay, lyophilizing the antibodies within a cassette used by the diagnostic device and/or sealing the cassette with a stabilizer and/or anticoagulant. The fifth embodiments or any other embodiments may include variants that includes adding disease-specific capture proteins on channel walls in the cassette via physisorption. The fifth embodiments or any other embodiments may include variants in which the adding includes using a stabilizing agent. The fifth embodiments or any other embodiments may include variants in which the cassette is delivered to an end user site where the assay is performed with buffers or reagents pre-loaded therein. The fifth embodiments or any other embodiments may include variants in which the reagents comprise a silver reagent.

In embodiments, the disclosed subject matter includes a system for performing a diagnostic method according to any of the above method embodiments.

In one or more sixth embodiment a diagnostic system includes a diagnostic device configured to perform an assay on a sample in a microfluidic channel and to apply a negative pressure to the microfluidic channel in response to manual actuation. The diagnostic device has a connector for interfacing with a smart-enabled device. The diagnostic device is configured to draw power and transmit data via the connector. The sixth embodiments or any other embodiments may include variants that include a sample chamber and reagent cassette includes at least the microfluidic channel. The sixth embodiments or any other embodiments may include variants in which the diagnostic device includes a manually displaceable bulb covering a pressure chamber with a spring therein, wherein the negative pressure is generated by manually depressing the bulb. The sixth embodiments or any other embodiments may include variants in which the diagnostic device includes a light source and a sensor arranged to detect light from the sample. The sixth embodiments or any other embodiments may include variants in which the connector includes an audio jack connector. The sixth embodiments or any other embodiments may include variants that include the smart-enabled device. The sixth embodiments or any other embodiments may include variants in which the smart-enabled device includes a smart phone with a touch screen, the diagnostic device being constructed such that the negative pressure is applied at the same time as the user views and accesses to the touch screen with a single hand. The sixth embodiments or any other embodiments may include variants in which the diagnostic device includes a rectifying circuit that converts an audio signal via the connector into DC power to power operation of the diagnostic device. The sixth embodiments or any other embodiments may include variants in which the diagnostic device includes a converter that converts data regarding the assay for frequency-shift keying transmission by the connector. The sixth embodiments or any other embodiments may include variants in which the smart-enabled device is configured with an application that controls operation of the diagnostic device and/or decodes the frequency-shift keying data transmission. The sixth embodiments or any other embodiments may include variants in which the diagnostic device is configured to simultaneously perform at least three assays on the sample for detecting different diseases. The sixth embodiments or any other embodiments may include variants in which the assay uses gold-labeled IgM antibodies. The sixth embodiments or any other embodiments may include variants in which the diagnostic device includes a cassette with the microfluidic channel, the antibodies being within the cassette, wherein the antibodies are lyophilized and/or the cassette is sealed with a stabilizer and/or anticoagulant prior to performing the assay. The sixth embodiments or any other embodiments may include variants in which walls of the microfluidic channel have disease-specific capture proteins thereon, the proteins being attached via physisorption. The sixth embodiments or any other embodiments may include variants in which the cassette is sealed with buffers or reagents prior to use in performing the assay. The sixth embodiments or any other embodiments may include variants in which the reagents comprise a silver reagent.

According to one or more embodiments, the disclosed subject matter includes a non-transitory computer-readable storage medium embodied with a sequence of programmed instructions, and a computer processing system that executes the sequence of programmed instructions embodied on the computer-readable storage medium to cause the computer processing system to perform the method of any of the above method embodiments or to control the system of any of the above system embodiments.

According to one or more further embodiment, a kit includes a least the reagent cassette and antibody holder of any of the above system or method claims.

In one or more seventh embodiments, a handheld diagnostic system includes a reagent cassette includes a microfluidic network having an inlet, an outlet, and a plurality of detection zones. An antibody holder has a plurality of labeled antibodies therein and an outlet configured to interface with the inlet of the reagent cassette to deliver the antibodies to the microfluidic network. A diagnostic dongle includes a recess, a pressure system, an array of light sources, an array of photodetectors, a control module, and an input/output connector. The detection zones are aligned with a respective light source and photodetector pair of the arrays when the cassette is inserted into the recess of the diagnostic dongle. The pressure system applies a negative pressure to the microfluidic network via the outlet of the reagent cassette to move fluids therethrough. The reagent cassette includes reagents and a lysis agent for whole blood. The cassette microfluidic network including converging channels to cause the reagents and lysis agent to mix with blood when drawn through a respective portion of the microfluidic network. The detection zones include at least a first detection zone as a hemoglobin testing zone with no antigens thereon, a second detection zone having an antigen specific for HIV thereon, and a third detection zone having an antigen specific for syphilis thereon. The light source and photodetector pair are aligned with the first detection zone includes a green-light-emitting light source and a green-sensitive photodetector. Each of the light source and photodetector pairs aligned with the second and third detection zones includes a red-light-emitting light source and a red-sensitive photodetector. The control module connected to the respective pairs of light sources and photodetectors to actuate them and whereby, in use, light from the first detection zone is emitted and received by a respective photodetector to permit a colorimetric assay and light is emitted from the second and third detection zones and received by one or more respective photodetectors to permit an immunoassay. Electrical power for the diagnostic dongle is provided exclusively via the input/output connector. The control module is configured to generate and transmit data representing results of the colorimetric assay and immunoassay via the input/output connector.

The seventh embodiments or any other embodiments may include variants that include a smartphone or personal digital assistant (PDA) that couples to the input/output connector to provide the electrical power and/or transmit data. The seventh embodiments or any other embodiments may include variants in which the input/output connector is configured to interface with an audio port or a USB port of the smartphone or PDA The seventh embodiments or any other embodiments may include variants in which the input/output connector includes an audio jack. The seventh embodiments or any other embodiments may include variants in which the diagnostic device and the smartphone or PDA are constructed to be held and operated by a user at the same time using a single hand. The seventh embodiments or any other embodiments may include variants in which the diagnostic device and the smartphone or PDA are constructed to be held and operated by a user at the same time using one hand to operate the pressure system and another hand to operate the smartphone or PDA. The seventh embodiments or any other embodiments may include variants in which the antigens in the second and third detection zones comprise disease-specific capture proteins that have been adhered to channel walls of the microfluidic network via physisorption. The seventh embodiments or any other embodiments may include variants in which the detection region further includes fourth and fifth detection zones operating as negative and positive control zones, respectively. The seventh embodiments or any other embodiments may include variants in which the positive control zone has rabbit anti-goat IgG antibody thereon and the negative control zone is free of antibodies. The seventh embodiments or any other embodiments may include variants in which the pressure system includes a manually displaceable bulb covering a pressure chamber with a spring therein, wherein the negative pressure is generated by manually depressing the bulb. The seventh embodiments or any other embodiments may include variants in which the labeled antibodies are gold-labeled antibodies. The seventh embodiments or any other embodiments may include variants in which the labeled antibodies include IgM antibodies. The seventh embodiments or any other embodiments may include variants in which the reagents comprise a silver reagent. The seventh embodiments or any other embodiments may include variants in which the reagents comprise silver nitrate and/or reducing agents. The seventh embodiments or any other embodiments may include variants in which the reagents and/or the lysis agent in the reagent cassette have been lyophilized prior to use in the diagnostic system. The seventh embodiments or any other embodiments may include variants in which the reagent cassette further includes a buffer therein. The seventh embodiments or any other embodiments may include variants in which the buffer includes bovine serum albumin (BSA) and/or polyoxyethylene sorbitan monopalmitate (TWEEN) in a phosphate buffered saline (PBS). The seventh embodiments or any other embodiments may include variants in which the lysis agent includes at least one of 3-[(3-cholamidopropyl)dimethyammonio]-1-propanesulfonate (CHAPS), sodium deoxycholate, and polyethylene glycol p-(1,1,3,3-tetramethylbutyl)-phenyl ether (TRITION X-100) in at least one of water and phosphate buffered saline (PBS). The seventh embodiments or any other embodiments may include variants in which the lysis agent includes 3-[(3-cholamidopropyl)dimethyammonio]-1-propanesulfonate (CHAPS) in phosphate buffered saline (PBS). The seventh embodiments or any other embodiments may include variants in which the light source aligned with the first detection zone emits light having a wavelength of 530 nm. The seventh embodiments or any other embodiments may include variants in which the light sources aligned with the second and third detection zones each emit light having a wavelength of 636 nm. The seventh embodiments or any other embodiments may include variants in which each of the light sources is a light-emitting diode (LEDs) or laser diode. The seventh embodiments or any other embodiments may include variants in which each of the photodetectors is a photodiode. The seventh embodiments or any other embodiments may include variants in which a pinhole aperture is provided in the optical path between each of the detection zones and its corresponding photodetector. The seventh embodiments or any other embodiments may include variants in which the detection zones share at least one light source or at least one photodetector forming the respective pairs such that fewer than three light sources and/or fewer than three photodetectors are provided.

In one or more eighth embodiments, an accessory for a handheld diagnostic system includes a reagent cassette that includes a microfluidic network having an inlet, an outlet, and a plurality of detection zones. An antibody holder is connectable to or integrated in the reagent cassette having a plurality of labeled antibodies therein and an outlet such as to connected or connectable to deliver the antibodies to the microfluidic network. The detection zones are spaced apart and distributed to so that opposite sides of each are accessible for the transmission of light through each the detection zones. The reagent cassette further includes reagents and a lysis agent for whole blood. The cassette microfluidic network including converging channels interconnected to permit the reagents and lysis agent to mix with blood when drawn through a respective portion of the microfluidic network. The detection zones include at least (1) a first detection zone as a hemoglobin testing zone with no antigens thereon, (2) a second detection zone having an antigen specific for HIV thereon, and (3) a third detection zone having an antigen specific for syphilis thereon.

The eighth embodiments or any other embodiments may include variants in which the cassette further includes fourth and fifth detection zones for use as negative and positive control zones, respectively. The eighth embodiments or any other embodiments may include variants in which the positive control zone has rabbit anti-goat IgG antibody thereon and the negative control zone is free of antibodies. The eighth embodiments or any other embodiments may include variants in which the labeled antibodies are gold-labeled antibodies. The eighth embodiments or any other embodiments may include variants in which the labeled antibodies include IgM antibodies. The eighth embodiments or any other embodiments may include variants in which the reagents comprise a silver reagent. The eighth embodiments or any other embodiments may include variants in which the reagents comprise silver nitrate and/or reducing agents. The eighth embodiments or any other embodiments may include variants in which the reagents and/or the lysis agent in the reagent cassette have been lyophilized prior to use in the accessory. The eighth embodiments or any other embodiments may include variants in which the reagent cassette further includes a buffer therein. The eighth embodiments or any other embodiments may include variants in which the buffer includes bovine serum albumin (BSA) and/or polyoxyethylene sorbitan monopalmitate (TWEEN) in a phosphate buffered saline (PBS). The eighth embodiments or any other embodiments may include variants in which the lysis agent includes at least one of 3-[(3-cholamidopropyl)dimethyammonio]-1-propanesulfonate (CHAPS), sodium deoxycholate, and polyethylene glycol p-(1,1,3,3-tetramethylbutyl)-phenyl ether (TRITION X-100) in at least one of water and phosphate buffered saline (PBS). The eighth embodiments or any other embodiments may include variants in which the lysis agent includes 3-[(3-cholamidopropyl)dimethyammonio]-1-propanesulfonate (CHAPS) in phosphate buffered saline (PBS).

In one or more ninth embodiments, a diagnostic method, includes mixing a lysis agent and whole blood in a fluid circuit and distributing the lysis agent and blood to multiple detection zones of the fluid circuit. The method further includes flowing respective reagents to the multiple detection zones. A first of the detection zones is a hemoglobin testing zone with no antigens thereon. A second of the detection zones has an antigen specific for HIV. A third of the detection zones has an antigen specific for a non-HIV disease. The method further includes simultaneously performing at least one of absorbance measurements, immunoassay, colorimetry, and electrochemical detection on samples in the detection zones.

The ninth embodiments or any other embodiments may include variants in which the mixing and distributing are performed using a microfluidic accessory attachable to a handheld multifunction device. The ninth embodiments or any other embodiments may include variants in which the handheld multifunction device includes a smartphone. The ninth embodiments or any other embodiments may include variants in which the mixing includes applying a vacuum to effect flow through the fluid circuit. The ninth embodiments or any other embodiments may include variants in which the third of the detection zones has an antigen specific for syphilis thereon. The ninth embodiments or any other embodiments may include variants that include further includes distributing the lysis agent and blood to a control detection zone. The ninth embodiments or any other embodiments may include variants in which the fluid circuit includes at least one microfluidic channel. The ninth embodiments or any other embodiments may include variants in which the mixing is effected by the distributing.

In one or more embodiments of the disclosed subject matter, the diagnostic device can use one or more of the following features, which may aid in achieving extremely-low power consumption:
 1. Mechanically-activated negative-pressure chamber; and
 2. Connection between diagnostic device and smartphone or personal digital assistant (PDA), for powering and data transmission.

By employing one or more of the above noted features, diagnostic devices according to embodiments of the disclosed subject matter may enjoy one or more of the following benefits:
 1. Diagnostic device can utilize very little power due to manual generation of negative-pressure source;
 2. Because of the lower power requirement, the diagnostic device can be completely powered by a smart-enabled device or small battery, thereby enabling a true point-of-care system that does not require a reliable power grid;

3. A user of the diagnostic device need only perform very simple steps in order to perform an otherwise complex assay.

Although specific examples of the diagnostic device for health care applications have been discussed, embodiments of the disclosed subject matter are not limited thereto. Rather, the diagnostic device can be applied to a wide range of applications according to one or more contemplated embodiments. For example, the diagnostic device may be useful in non-medical scenarios, such as, but not limited to, environmental and soil testing, food safety testing, and water quality testing.

In any of the embodiments, a system can be configured to perform any method disclosed herein.

In any of the embodiments, a non-transitory computer-readable storage medium is embodied with a sequence of programmed instructions, and a computer processing system executes the sequence of programmed instructions embodied on the computer-readable storage medium to cause the computer processing system to perform any of the methods disclosed herein.

It will be appreciated that the modules, processes, systems, and devices described above can be implemented in hardware, hardware programmed by software, software instruction stored on a non-transitory computer readable medium or a combination of the above. For example, a method for performing a diagnosis can be implemented, for example, using a processor configured to execute a sequence of programmed instructions stored on a non-transitory computer readable medium. For example, the processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and devices can be implemented as a single processor or as a distributed processor. Further, it should be appreciated that the steps mentioned herein may be performed on a single or distributed processor (single and/or multi-core). Also, the processes, modules, and sub-modules described in the various figures of and for embodiments herein may be distributed across multiple computers or systems or may be co-located in a single processor or system. Structural embodiment alternatives suitable for implementing the modules, systems, or processes described herein are provided below.

The modules, processes, systems, and devices described above, for example, the control unit, can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the methods, processes, modules, devices, and systems (or their sub-components or modules) may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the methods, systems, or computer program products (software program stored on a non-transitory computer readable medium).

Furthermore, embodiments of the disclosed methods, processes, modules, devices, systems, and computer program product may be readily implemented, fully or partially, in software using, for example, object or object-oriented software development environments that provide portable source code that can be used on a variety of computer platforms. Alternatively, embodiments of the disclosed methods, processes, modules, devices, systems, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the methods, processes, modules, devices, systems, and computer program product can be implemented in hardware and/or software using any known or later developed systems or structures, devices and/or software by those of ordinary skill in the art from the function description provided herein and with knowledge of diagnostic systems and/or computer programming arts.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, low-cost handheld extremely-low power diagnostic devices, systems, and methods. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. A handheld diagnostic system, comprising:
   a reagent cassette comprising a microfluidic network having an inlet, an outlet, and a detection region, the detection region including at least one detection zone; and
   a diagnostic dongle comprising a recess, a manually-actuated pressure system configured to generate negative pressure and store the negative pressure in a pressure chamber, at least one light source, at least one photodetector, a control module, and an input/output connector; and
   a smartphone or personal digital assistant (PDA) coupled to the input/output connector of the diagnostic dongle and configured to provide electrical power to the diagnostic dongle and to transmit data from the diagnostic dongle;
   wherein the at least one detection zone is aligned with a respective photodetector when the reagent cassette is inserted into the recess of the diagnostic dongle;
   wherein the manually-actuated pressure system is configured to apply the negative pressure to the microfluidic network of the reagent cassette to move fluids therethrough;
   wherein the reagent cassette includes reagents and/or a lysis agent for whole blood; and
   wherein the control module is programmed to control the at least one light source and the at least one photodetector to interrogate the respective detection zone to perform at least one of a colorimetric assay, an immunoassay, an electrochemical assay, and absorbance detection.

2. The diagnostic system of claim 1, wherein the input/output connector is configured to interface with an audio port or a USB port of the smartphone or PDA.

3. The diagnostic system of claim 2, wherein the input/output connector comprises an audio jack.

4. The diagnostic system of claim 1, wherein the diagnostic dongle and the smartphone or PDA are constructed to be held and operated by a user at the same time using a single hand.

5. The diagnostic system of claim 1, wherein the diagnostic dongle and the smartphone or PDA are constructed to be held and operated by a user at the same time using one hand to operate the manually-actuated pressure system and another hand to operate the smartphone or PDA.

6. The diagnostic system of claim 1, wherein electrical power for the diagnostic dongle is provided exclusively via said input/output connector.

7. The diagnostic system of claim 1, wherein the control module is configured to convert data of results of the colorimetric assay and immunoassay by frequency-shift keying (FSK) and to transmit FSK-converted data via the input/output connector.

8. The diagnostic system of claim 1, further comprising an antibody holder having a plurality of labeled antibodies therein and an outlet configured to interface with the inlet of the reagent cassette to deliver the antibodies to the microfluidic network.

9. The diagnostic system of claim 1, wherein antigens in the at least one detection zone comprise disease-specific capture proteins that have been adhered to channel walls of the microfluidic network via physisorption.

10. The diagnostic system of claim 1, wherein the detection region further includes detection zones operating as negative and positive control zones.

11. The diagnostic system of claim 1, wherein the manually-actuated pressure system comprises a manually displaceable bulb covering the pressure chamber with a spring therein, wherein said negative pressure is generated by manually depressing said bulb to compress the spring and subsequently the spring exerting a force on the manually displaceable bulb.

12. The diagnostic system of claim 10, wherein a pinhole aperture is provided in an optical path between each of the detection zones and its corresponding photodetector.

13. The diagnostic system of claim 1, wherein the manually-actuated pressure system applies a negative pressure to the microfluidic network.

14. A diagnostic method, comprising:
   using one hand to hold and manually actuate a manually-actuated pressure system of a diagnostic device to generate a negative pressure and store the negative pressure in a pressure chamber, and which pulls a sample into a detection zone of a reagent cassette;
   performing an assay on the sample in the detection zone to generate data; and
   transmitting said data from the diagnostic device to a smart-enabled device via a connection dongle disposed between the diagnostic device and the smart-enabled device while also receiving power for the diagnostic device via said connection dongle.

15. The diagnostic method of claim 14, wherein the manually-actuated pressure system to generate the negative pressure comprises a bulb covering a pressure chamber with a spring therein, wherein said negative pressure is generated by depressing said bulb.

16. The diagnostic method of claim 14, wherein the connection dongle between the diagnostic device and the smart-enabled device comprises an audio jack.

17. The diagnostic method of claim 14, wherein the transmitting said data comprises converting the data via frequency-shift keying for transmission via said connection dongle.

18. The diagnostic method of claim 14 wherein the assay includes at least one of absorbance measurements, immunoassay, colorimetry, and electrochemical detection.

19. The diagnostic method of claim 14, wherein the assay comprises a diagnostic test for at least one of human immunodeficiency virus (HIV), syphilis, anemia, glucose, total protein, and serum iron.

20. The diagnostic method of claim 14, wherein the diagnostic device obtains all of its electrical power requirements via the power received via the connection dongle.

21. The diagnostic method of claim 14, wherein at least three assays for detecting different diseases are simultaneously performed on the sample.

22. The diagnostic method of claim 14, wherein the assay uses gold-labeled IgM antibodies.

23. The diagnostic method of claim 22, further comprising, prior to the performing an assay, lyophilizing the antibodies within the reagent cassette used by the diagnostic device and/or sealing the reagent cassette with a stabilizer and/or anticoagulant.

24. The diagnostic method of claim 14, further comprising adding disease-specific capture proteins on channel walls in the reagent cassette via physisorption.

* * * * *